US012780882B2

(12) United States Patent
Goldberg et al.

(10) Patent No.: US 12,780,882 B2
(45) Date of Patent: Nov. 3, 2026

(54) METHODS OF TREATING, AMELIORATING, AND/OR PREVENTING COVID-19 INFECTION AND RELATED INFLAMMATION

(71) Applicant: Rowan University, Glassboro, NJ (US)

(72) Inventors: Gary S. Goldberg, Voorhees, NJ (US); Paola Leone, Cherry Hill, NJ (US)

(73) Assignee: Rowan University, Glassboro, NJ (US)

(*) Notice: Subject to any disclaimer, the term of this patent is extended or adjusted under 35 U.S.C. 154(b) by 721 days.

(21) Appl. No.: 18/032,018

(22) PCT Filed: Oct. 19, 2021

(86) PCT No.: PCT/US2021/055542

§ 371 (c)(1),
(2) Date: Apr. 14, 2023

(87) PCT Pub. No.: WO2022/086916

PCT Pub. Date: Apr. 28, 2022

(65) Prior Publication Data

US 2023/0391837 A1 Dec. 7, 2023

Related U.S. Application Data

(60) Provisional application No. 63/093,911, filed on Oct. 20, 2020.

(51) Int. Cl.

*C07K 14/42* (2006.01)
*A61K 36/48* (2006.01)
*A61K 45/06* (2006.01)
*A61P 29/00* (2006.01)
*A61P 31/14* (2006.01)

(52) U.S. Cl.

CPC .............. *C07K 14/42* (2013.01); *A61K 36/48* (2013.01); *A61K 45/06* (2013.01); *A61P 29/00* (2018.01); *A61P 31/14* (2018.01)

(58) Field of Classification Search

CPC ........ C07K 14/42; A61K 36/48; A61K 45/06; A61K 38/168; A61K 38/00; A61P 29/00; A61P 31/14

See application file for complete search history.

(56) References Cited

U.S. PATENT DOCUMENTS

| | | | |
|---|---|---|---|
| 8,114,593 B2 | 2/2012 | Goldberg et al. | |
| 9,169,327 B2 | 10/2015 | Goldberg et al. | |
| 9,809,631 B2 | 11/2017 | Goldberg et al. | |
| 10,213,481 B2 | 2/2019 | Mayan Santos et al. | |
| 2012/0010152 A1* | 1/2012 | Goldberg ............ | A61K 38/178 435/375 |
| 2016/0207968 A1 | 7/2016 | Goldberg et al. | |
| 2016/0375096 A1 | 12/2016 | Mayan Santos et al. | |

FOREIGN PATENT DOCUMENTS

WO 2010093804 A1 8/2010

OTHER PUBLICATIONS

Yousra A. El-Maradny, ectins purified from medicinal and edible mushrooms: Insights into their antiviral activity against pathogenic viruses, International Journal of Biological Macromolecules 179 (2021) 239-258.*

Liu et al., A Carbohydrate-Binding Protein from the Edible Lablab Beans Effectively Blocks the Infections of Influenza Viruses and SARS-CoV-2, Aug. 2020, Cell Reports 32, 108016.*

Sheehan, et al., "Evidence that Maackia amurensis seed lectin (MASL) exerts pleiotropic actions on oral squamous cells with potential to inhibit SARS-CoV-2 infection and COVID-19 disease progression", Experimental Cell Research, vol. 403, published online Apr. 3, 2021, 112594, 7 pages.

Smeda, et al., "Endothelial barrier integrity in COVID-19-dependent hyperinflammation: does the protective facet of platelet function matter?", Cardiovasc Res, vol. 116, No. 10, 2020, pp. e118-e121.

International Search Report & Written Opinion dated Feb. 2, 2022 for corresponding PCT International Application PCT/US2021/055542.

* cited by examiner

*Primary Examiner* — Erinne R Dabkowski

(74) *Attorney, Agent, or Firm* — Saul Ewing LLP; Domingos J. Silva; Chihao Wang

(57) ABSTRACT

The present disclosure relates in part to methods of treating, preventing, and/or ameliorating SARS-CoV-2 infection and/or related inflammatory syndromes by administration of a *Maackia amurensis* seed lectin (MASL). MASL has a strong affinity for sialic acid modified proteins and may be used as an antiviral agent. This lectin targets the ACE2 receptor, decreases ACE2 expression and glycosylation, suppresses binding of the SARS-CoV-2 spike protein, and decreases expression of inflammatory mediators by oral epithelial cells that cause ARDS in COVID-19 patients.

6 Claims, 23 Drawing Sheets

Specification includes a Sequence Listing.

Profile

MASL + ACE2

METHODS OF TREATING, AMELIORATING, AND/OR PREVENTING COVID-19 INFECTION AND RELATED INFLAMMATION

CROSS-REFERENCE TO RELATED APPLICATIONS

The present application is a 35 U.S.C. § 371 national phase application of, and claims priority to, International Application No. PCT/US2021/055542, filed Oct. 19, 2021, which claims priority under 35 U.S.C. § 119 (e) to U.S. Provisional Patent Application No. 63/093,911, filed Oct. 20, 2020, the disclosures of which are incorporated herein by reference in their entireties.

STATEMENT REGARDING FEDERALLY SPONSORED RESEARCH

This invention was made with government support under CA235347 awarded by the National Institutes of Health. The government has certain rights in the invention.

SEQUENCE LISTING

The ASCII text file named "370431-1027WO1 Seq Listing" created on Oct. 5, 2021, comprising 3 Kbytes, is hereby incorporated by reference in its entirety.

BACKGROUND

COVID-19 was declared an international public health emergency in January 2020, and a pandemic in March 2020. There are over 219 million confirmed COVID-19 cases, causing over 4.55 million deaths worldwide as of Oct. 10, 2021. The situation is dire in the US, with over 44.3 million cases and 714 thousand deaths as of October 2021. Over 23 thousand new cases were reported in the US during the week of Oct. 10, 2021, with 481 deaths. The standard of care for COVID-19 is supportive treatment, as there is no approved specific treatment for COVID-19 nor any drug or vaccine that can be used to prevent COVID-19 disease in humans.

Thus, there is a need in the art for new treatment and prevention options for COVID-19 and/or any COVID-19-associated complications and/or symptoms, and the present disclosure addresses this need.

BRIEF SUMMARY OF INVENTION

The present invention relates to, but is not limited to, compositions and methods for treating, ameliorating, and/or preventing a SARS-CoV-2 infection, COVID-19, and/or any complications and/or symptoms associated with SARS-CoV-2 infection and/or COVID-19.

The instant specification is also directed to, but not limited to, the following non-limiting embodiments:

Embodiment 1, a method of decreasing ACE2 expression and/or glycosylation in a subject, the method comprising administering to the subject a pharmaceutical composition comprising at least one pharmaceutically acceptable carrier and a therapeutically effective amount of a lectin.

Embodiment 2, the method of embodiment 1, wherein the lectin is a Maacki amurensis seed lectin (MASL).

Embodiment 3, the method of embodiment 1 or 2, wherein the lectin comprises an amino acid sequence having about 90 percent similarity or more to the amino acid sequence of SEQ ID NO:1.

Embodiment 4, the method of embodiment 2, wherein the MASL comprises an amino acid sequence having SEQ ID NO:1 or a biologically active fragment thereof.

Embodiment 5, a method of treating, preventing, and/or ameliorating a SARS-CoV-2 infection, the method comprising administering to the subject a pharmaceutical composition comprising at least one pharmaceutically acceptable carrier and a therapeutically effective amount of a lectin.

Embodiment 6, the method of embodiment 5, wherein the lectin is a Maacki amurensis seed lectin (MASL).

Embodiment 7, the method of embodiment 5 or 6, wherein the lectin comprises an amino acid sequence having about 90 percent similarity or more to the amino acid sequence of SEQ ID NO:1.

Embodiment 8, the method of embodiment 6, wherein the MASL comprises an amino acid sequence having SEQ ID NO:1 or a biologically active fragment thereof.

Embodiment 9, the method of any of embodiments 5-8, further comprises administering to the subject a therapeutically effective amount of a second agent effective for treating, preventing, and/or ameliorating the SARS-CoV-2 infection.

Embodiment 10, the method of embodiment 9, wherein the second agent comprises at least one selected from the group consisting of an antiviral agent, an anti-SARS-CoV-2 antibody, and an immunomodulator.

Embodiment 11, the method of any of embodiments 5-10, wherein the SARS-CoV-2 infection causes cytokine storm or acute respiratory distress syndrome (ARDS) in the subject.

Embodiment 12, the method of any of embodiments 5-11, wherein the subject is a human.

Embodiment 13, a method of treating, ameliorating, and/or preventing inflammation in a subject, the method comprising administering to the subject a pharmaceutical composition comprising at least one pharmaceutically acceptable carrier and a therapeutically effective amount of a lectin.

Embodiment 14, the method of embodiment 13, wherein the lectin is a Maacki amurensis seed lectin (MASL).

Embodiment 15, the method of embodiment 13 or 14, wherein the lectin comprises an amino acid sequence having about 90 percent similarity or more to the amino acid sequence of SEQ ID NO:1.

Embodiment 16, the method of embodiment 14, wherein the MASL comprises an amino acid sequence having SEQ ID NO:1 or a biologically active fragment thereof.

Embodiment 17, the method of any of embodiments 13-16, wherein the inflammation is caused by overexpression of at least one selected from the group consisting of disintegrin and metalloprotease 17 (ADAM17), nuclear factor kappa-light-chain-enhancer of activated B cells (NFκB), signal transducer and activator of transcription 3 (STAT3), TNF superfamily member 10 (TNFSF10), toll-like receptor 3 (TLR3)m and toll-like receptor 4 (TLR4), Embodiment 18, the method of any of embodiments 13-17, wherein the inflammation is caused by at least one viral infection selected from the group consisting of a SARS-CoV infection, a MERS-CoV infection, a SARS-CoV-2 infection, and an influenza virus infection.

Embodiment 19, the method of any of embodiments 13-18, wherein the inflammation comprises a cytokine storm or acute respiratory distress syndrome (ARDS) caused by a SARS-CoV-2 infection.

Embodiment 20, the method of any of embodiments 13-19, wherein the subject is a human.

BRIEF DESCRIPTION OF THE FIGURES

The drawings illustrate generally, by way of example, but not by way of limitation, various embodiments of the present application.

FIG. 4A: HSC2 OSCC cells incubated with fluorescently labeled MASL for 2 minutes and examined by confocal microscopy. FIG. 4B: HSC2 cells incubated with MASL (red) for 2 minutes (red), washed, stained with PDPN antibody (green), Hoechst (blue), and examined by DIC and confocal microscopy. Colocalization of MASL and PDPN (yellow) is apparent in this merged image, including orthogonal z-axis views as described.

FIG. 7A: HSC2 cells treated with 0, 770, or 1925 nM MASL for 12 hours were examined by RNA-Seq. Data are shown as percent of untreated controls (mean±SEM, n=2) and p values by ANOVA. FIG. 7B: MASL inhibition of specific glycosylases.

FIG. 9A: HSC2 cells treated with 0, 770, or 1925 nM MASL for 12 hours were examined by Western blotting with anitbodies specific for ACE2, STAT1, phosphorylated at Tyr701, and β-actin, as indicated. Glycosylated and primary full length protein migrate at 120 kD and 92 kD, respectively. FIG. 9B: Data are shown as percent of untreated controls (mean±SEM, n=2) with asterisks indicating p<0.05 compared to untreated controls by t-test.

FIG. 10A: HSC2 cells incubated with 2 μM fluorescently labeled spike protein (Alexa Fluor 555) for 1 hour with and without 1.4 μM MASL examined by confocal microscopy as indicated (bar=200 microns). FIG. 10B: SARS-CoV-2 S1 (genbank QHD43416 Val 16—Gln690) produced by HEK 293 cells migrates at ~120 kD (lane 2), and ~75 kD (lanes 3,4) after glycosylase treatment (RayBiotech #230-30161).

FIG. 14A: Inflammatory pathways triggered by COVID-19 infections are indicated along with potential effects of MASL. FIG. 14B: HSC2 cells treated with 0, 770, or 1925 nM MASL for 12 hours were examined by RNA-Seq. Data are shown as percent of untreated controls (mean±SEM, n=2). Single, double, triple asterisks, and ns indicate p values <0.05, <0.01, <0.001, and >0.05 by ANOVA, respectively.

FIG. 15A: HSC-2 cells were incubated with 0.4 mg/ml Alexa 647 labeled ACE2 monoclonal antibody and 1.4 μM Alexa 595 labeled MASL and examined by live cell confocal microscopy. Fluorescent, DIC, and merged images are shown as indicated (bar=100 μm). FIG. 15B: orthogonal imaging of MASL and ACE2 colocalization in cut out view indicated by arrows (bar=20 μm). FIG. 15C: intensity plot profile over distance in one focal plane of an observed area as indicated. FIG. 15D: cells were incubated with 2 μM Alexa 555 labeled spike protein for 1 h with and without 1.4 μM MASL. Fluorescent, DIC, and merged images are shown as indicated (bar=200 μm). FIG. 15E: fluorescence from a 15000 $\mu m^2$ area of cells incubated with spike protein with and without MASL was quantitated with quadruple asterisks indicating p<0.0001 by t-test and indicated (mean±SEM, n=4).

In FIGS. 16A-16C, HSC-2 cells were treated for 12 h with 0, 770, or 1925 nM MASL and examined by RNA-Seq. Expression of gene transcripts were quantitated and shown as percent of untreated control cells (mean±SEM, n=2) with p values by ANOVA as indicated. FIG. 16A demonstrates that MASL inhibits ACE2, ADAM17, and furin mRNA levels, in accordance with some embboddiments. FIG. 16B demonstrates that MASL inhibits mRNA levels of glycosylases (C1galt, St6galnac1, and St6galnac2) needed for sialic acid modification of the ACE2 receptor, in accordance with some embodiments. FIG. 16C demonstrates that MASL increases expression of anti-inflammatory transcripts (Hmox1 and Il36rn), and decreases expression of pro-inflammatory (Nfkb1, Foxo1, Tnfsf10, Tlr4, and Tlr3) mRNA transcripts, in accordance with some embodiments.

FIG. 17A: HSC-2 cells were treated for 12 h with 0, 770, or 1925 nM MASL and examined by Western blotting with apparent molecular weights shown as indicated. Primary and glycosylated ACE2 protein are evident at 92 and 120 kD, respectively FIG. 17B: protein expression was quantitated by image densitometry and shown as percent of untreated control cells (mean±SEM, n=3) with p values by ANOVA as indicated.

FIG. 18A: HeLa cells transfected with Luciferase reporter constructs to detect NFκB and STAT3 activity were incubated with 0, 3.08, 5.16, or 7.70 μM MASL for 4-6 h, as indicated. Luminescence values were normalized to untreated non-transfected control cells and are shown as percent control (mean±SEM, n=2) with p values by ANOVA as indicated. FIG. 18B: Vero E6 cells were incubated SARS-COV-2 virus for 72 h in 0, 770, and 2310 nM MASL. Cell viability was measured and shown as percent control (mean±SEM, n=4) with quadruple asterisk indicating $p<0.0001$ by ANOVA as indicated. FIG. 18C is a diagram illustrating how MASL reduces ACE2, ADAM17, and furin expression, and decreases inflammatory signaling events that would otherwise lead to activation of the IL6 amplifier implicated in COVID-19 induced ARDS.

DETAILED DESCRIPTION OF THE INVENTION

Figure 1:
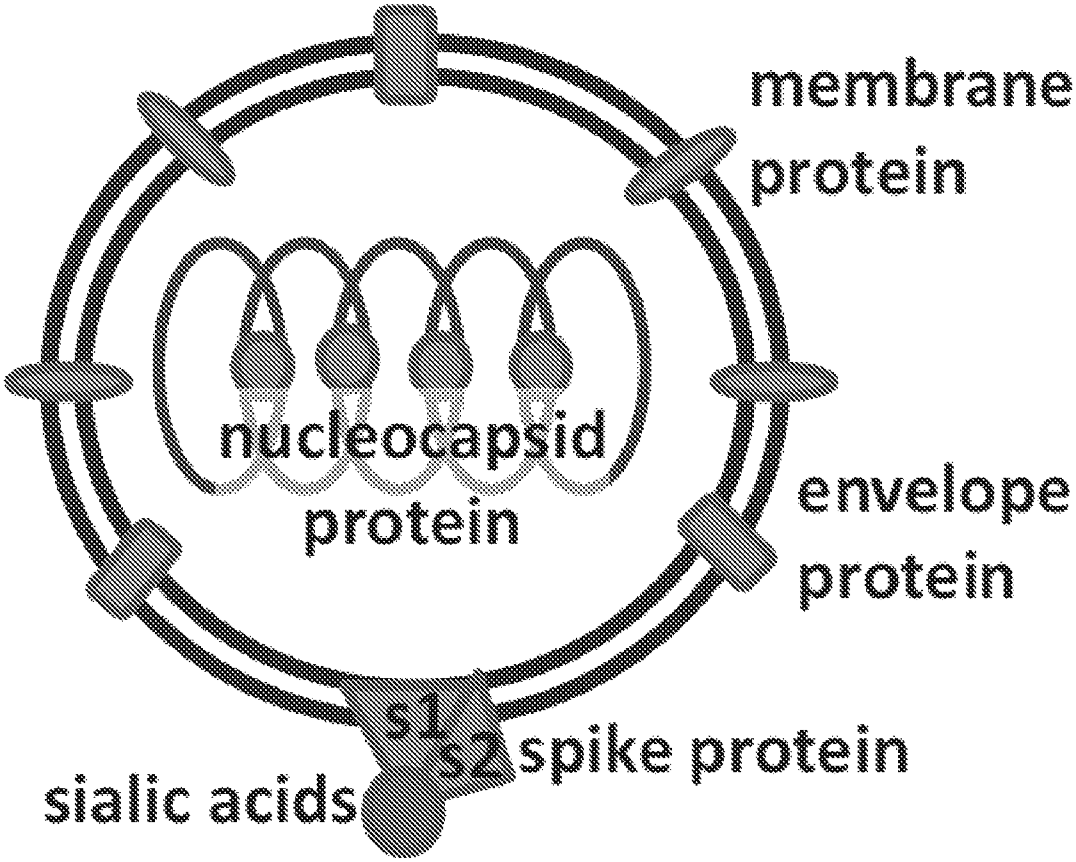
FIG. 1 shows the SARS-CoV-2 structure: schematic of genomic RNA with nucleocapsid protein package in a membrane with membrane, envelope proteins, and sialic acid modified spike protein that targets host ACE2 receptors.

Reference will now be made in detail to certain embodiments of the disclosed subject matter, examples of which are illustrated in part in the accompanying drawings. While the disclosed subject matter will be described in conjunction with the enumerated claims, it will be understood that the exemplified subject matter is not intended to limit the claims to the disclosed subject matter.

Throughout this document, values expressed in a range format should be interpreted in a flexible manner to include not only the numerical values explicitly recited as the limits of the range, but also to include all the individual numerical values or sub-ranges encompassed within that range as if each numerical value and sub-range is explicitly recited. For example, a range of "about 0.1% to about 5%" or "about 0.1% to 5%" should be interpreted to include not just about 0.1% to about 5%, but also the individual values (e.g., 1%, 2%, 3%, and 4%) and the sub-ranges (e.g., 0.1% to 0.5%, 1.1% to 2.2%, 3.3% to 4.4%) within the indicated range. The statement "about X to Y" has the same meaning as "about X to about Y," unless indicated otherwise. Likewise, the statement "about X, Y, or about Z" has the same meaning as "about X, about Y, or about Z," unless indicated otherwise.

U.S. Pat. Nos. 10,213,481, 9,809,631, 9,169,327, and 8,114,593 are each incorporated by reference herein in their entireties.

In the methods described herein, the acts can be carried out in any order, except when a temporal or operational sequence is explicitly recited. Furthermore, specified acts can be carried out concurrently unless explicit claim language recites that they be carried out separately. For example, a claimed act of doing X and a claimed act of doing Y can be conducted simultaneously within a single operation, and the resulting process will fall within the literal scope of the claimed process.

COVID-19 is caused by the SARS-CoV-2 virus. SARS-CoV-2 is an RNA virus with a surface "spike" protein that binds to the angiotensin converting enzyme (ACE2) receptor to infect cells. In addition to the respiratory tract, SARS-CoV-2 also infects oral mucosal cells, which also express ACE2. The ACE2 receptor, associated membrane gangliosides, and viral spike protein are all highly glycosylated with sugars including sialic acids that direct viral-host interactions needed for infection. Lectins recognize specific glycosylation motifs, and can be used as antiviral agents. In particular *Maackia amurensis* seed lectin (MASL) has a strong affinity for sialic acid modified proteins, and targets specific receptors to inhibit viral infection, cancer progression, and inflammation.

The study described herein includes a pilot study and a follow-up comprehensive study (which are referred to "the present study" collectively herein). As described elsewhere herein, using human oral squamous cell carcinoma (OSCC) cells and SARS-CoV-2 virus as a non-limiting illustrative examples, the pilot study demonstrates that MASL targets the ACE2 receptor and inhibits SARS-CoV-2 spike binding, which is need for the viral attachment. The pilot study further demonstrates that MASL decreases the expression of ACE2 (which serves as the entry point into cells for some coronaviruses, including SARS-CoV-2), furin (which promotes virial cell entry by cleaving a polybasic sequence to unlink the S1 and S2 domains in the SARS spike protein), and sialic acid glycosylases. The pilot study further demonstrates that MASL decreases the expression of inflammatory cytokines, which are involved in cytokine storm syndrome (CSS) and associated acute respiratory distress syndrome (ARDS) that causes many COVID-19 deaths, as well as inflammatory conditions considered to be sequelae of COVID-19 infections. The comprehensive study confirmed the results of the pilot study with additional consistent experimental data.

Lectins are found in virtually all foods, and the vast majority of the known lectins are safe to consume. Lectins are resistant to gastrointestinal proteolysis, and can be administered orally to treat disease. As such, administering lectins, such as MASL, to subjects is relatively safe and easy.

Accordingly, in some aspects, the present invention is directed to a method of decreasing ACE2 expression and/or glycosylation in a subject. The method includes administering to the subject a pharmaceutical composition comprising at least one pharmaceutically acceptable carrier and a therapeutically effective amount of a lectin, such as a *Maackia amurensis* seed lectin (MASL).

In some aspects, the present invention is directed to a method of treating, ameliorating and/or preventing a viral infection in a subject in need thereof. The method includes administering to the subject a pharmaceutical composition comprising at least one pharmaceutically acceptable carrier and a therapeutically effective amount of a lectin, such as a *Maackia amurensis* seed lectin (MASL). In some embodiments, the viral infection is a coronavirus infection, such as a SARS-CoV-2 infection.

In some aspects, the present invention is directed to a method of decreasing inflammation in a subject. The method includes administering to the subject a pharmaceutical composition comprising at least one pharmaceutically acceptable carrier and a therapeutically effective amount of a lectin, such as a *Maackia amurensis* seed lectin (MASL). In some embodiments, the inflammation includes a cytokine storm or an acute respiratory distress syndrome (ARDS). In some embodiments, the inflammation is caused by a SARS-CoV-2 infection.

Definitions

In this document, the terms "a," "an," or "the" are used to include one or more than one unless the context clearly dictates otherwise. The term "or" is used to refer to a nonexclusive "or" unless otherwise indicated. The statement "at least one of A and B" or "at least one of A or B" has the same meaning as "A, B, or A and B." In addition, it is to be understood that the phraseology or terminology employed herein, and not otherwise defined, is for the purpose of description only and not of limitation. Any use of section headings is intended to aid reading of the document and is not to be interpreted as limiting; information that is relevant to a section heading may occur within or outside of that particular section. All publications, patents, and patent documents referred to in this document are incorporated by reference herein in their entirety, as though individually incorporated by reference.

The term "about" as used herein can allow for a degree of variability in a value or range, for example, within 10%, within 5%, or within 1% of a stated value or of a stated limit of a range, and includes the exact stated value or range.

As used herein, the term "antiviral agent" means a composition of matter that, when delivered to a cell, is capable of preventing replication of a virus in the cell, preventing infection of the cell by a virus, or reversing a physiological effect of infection of the cell by a virus. Antiviral agents are well known and described in the literature. By way of example, AZT (zidovudine, RETROVIR®, Glaxosmithkline, Middlesex, UK) is an antiviral agent that is thought to prevent replication of HIV in human cells.

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

The phrase "inhibit" as used herein, means to reduce a molecule, a reaction, an interaction, a gene, an mRNA, and/or a protein's expression, stability, function or activity by a measurable amount or to prevent entirely. Inhibitors are compounds that, e.g., bind to, partially or totally block stimulation, decrease, prevent, delay activation, inactivate, desensitize, or down regulate a protein, a gene, and an mRNA stability, expression, function and activity, e.g., antagonists.

As used herein, the term "pharmaceutically acceptable" refers to a material, such as a carrier or diluent, which does not abrogate the biological activity or properties of the compound useful within the invention, and is relatively non-toxic, i.e., the material may be administered to a subject without causing undesirable biological effects or interacting in a deleterious manner with any of the components of the composition in which it is contained.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the subject such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the subject. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. As used herein, "pharmaceutically acceptable carrier" also includes any and all coatings, antibacterial and antifungal agents, and absorption delaying agents, and the like that are compatible with the activity of the compound useful within the invention, and are physiologically acceptable to the subject. Supplementary active compounds may also be incorporated into the compositions. The "pharmaceutically acceptable carrier" may further include a pharmaceutically acceptable salt of the compound useful within the invention. Other additional ingredients that may be included in the pharmaceutical compositions used in the practice of the invention are known in the art and described, for example in Remington's Pharmaceutical Sciences (Genaro, Ed., Mack Publishing Co., 1985, Easton, PA), which is incorporated herein by reference.

As used herein, the language "pharmaceutically acceptable salt" refers to a salt of the administered compound prepared from pharmaceutically acceptable non-toxic acids and/or bases, including inorganic acids, inorganic bases, organic acids, inorganic bases, solvates (including hydrates) and clathrates thereof.

The terms "pharmaceutically effective amount" and "effective amount" refer to a non-toxic but sufficient amount of an agent to provide the desired biological result. That result can be reduction and/or alleviation of the signs, symptoms, or causes of a disease or disorder, or any other desired alteration of a biological system.

As used herein, the terms "RT-PCR" or "reverse transcription polymerase chain reaction" refer to a laboratory technique combining reverse transcription of the RNA present in a sample to DNA, with amplification of specific DNA targets using the polymerase chain reaction. These terms may also refer to real time PCR, wherein the amplification of the DNA target is monitored and quantified by at least one of several detection methods, such methods comprising non-specific fluorescent dye intercalation with DNA and sequence-specific DNA probes consisting of oligonucleotides labeled with a fluorescent reporter, wherein fluorescence is detected only upon hybridization of the probe with its complementary sequence.

By the term "specifically binds" as used herein, is meant a molecule, such as an antibody, which recognizes and binds to another molecule or feature, but does not substantially recognize or bind other molecules or features in a sample.

The terms "subject" or "patient" or "individual" for the purposes of the present disclosure includes humans and other animals, particularly mammals, and other organisms. Thus the methods are applicable to both human therapy and veterinary applications.

The term "substantially" as used herein refers to a majority of, or mostly, as in at least about 50%, 60%, 70%, 80%, 90%, 95%, 96%, 97%, 98%, 99%, 99.5%, 99.9%, 99.99%, or at least about 99.999% or more, or 100%. The term "substantially free of" as used herein can mean having none or having a trivial amount of, such that the amount of material present does not affect the material properties of the composition including the material, such that the composition is about 0 wt % to about 5 wt % of the material, or about 0 wt % to about 1 wt %, or about 5 wt % or less, or less than, equal to, or greater than about 4.5 wt %, 4, 3.5, 3, 2.5, 2, 1.5, 1, 0.9, 0.8, 0.7, 0.6, 0.5, 0.4, 0.3, 0.2, 0.1, 0.01, or about 0.001 wt % or less. The term "substantially free of" can mean having a trivial amount of, such that a composition is about 0 wt % to about 5 wt % of the material, or about 0 wt % to about 1 wt %, or about 5 wt % or less, or less than, equal to, or greater than about 4.5 wt %, 4, 3.5, 3, 2.5, 2, 1.5, 1, 0.9, 0.8, 0.7, 0.6, 0.5, 0.4, 0.3, 0.2, 0.1, 0.01, or about 0.001 wt % or less, or about 0 wt %.

The terms "treat," "treating," and "treatment," refer to one or more therapeutic or palliative measures described herein. The methods of "treatment" employ administration to a subject, in need of such treatment, a composition, for example, a subject afflicted with a disease or disorder, or a subject who has one or symptoms of such a disease or disorder, in order to cure, delay, reduce the severity of, or ameliorate one or more symptoms of the disorder or recurring disorder, or in order to prolong the survival of a subject beyond that expected in the absence of such treatment.

The term "independently selected from" as used herein refers to referenced groups being the same, different, or a mixture thereof, unless the context clearly indicates otherwise. Thus, under this definition, the phrase "$X^1$, $X^2$, and $X^3$ are independently selected from noble gases" would include the scenario where, for example, $X^1$, $X^2$, and $X^3$ are all the same, where $X^1$, $X^2$, and $X^3$ are all different, where $X^1$ and $X^2$ are the same but $X^3$ is different, and other analogous permutations.

The term "room temperature" as used herein refers to a temperature of about 15° C. to 28° C.

The term "atm" as used herein refers to a pressure in atmospheres under standard conditions. Thus, 1 atm is a pressure of 101 kPa, 2 atm is a pressure of 202 kPa, and so on.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6, etc., as well as individual numbers within that range, for example, 1, 2, 2.7, 3, 4, 5, 5.3, and 6.

Method of Decreasing ACE2 Expression and/or Glycosylation

As described elsewhere herein, the study as described in the specification (also referred to as "the present study"), using Maacki amurensis seed lectin (MASL) and HSC-2 cell line as illustrative non-limiting examples, demonstrates that lectins are able to decrease the expressions of angiotensin-converting enzyme 2 (ACE2) and glycosylases responsible for sialic acid modification of ACE2.

SARS-CoV-2 virus, the causative agent of COVID-19, interacts with the ACE2, as well as the sialic acid residues on ACE2, on the surface of a host cell via the spike protein of the SARS-Cov2 virus. This interaction is required for the virus to enter and infect the host cell.

Therefore, in some aspects, the present invention is directed to a method of decreasing ACE2 expression and/or glycosylation in a subject. The method includes administering to the subject a pharmaceutical composition comprising at least one pharmaceutically acceptable carrier and a therapeutically effective amount of a lectin. Pharmaceutically acceptable carriers are known in the art and/or described elsewhere herein.

In some embodiments, the lectin is a Maacki amurensis seed lectin (MASL). In some embodiments, the MASL comprises the amino acid sequence of SEQ ID NO:1, or a biologically active fragment thereof. In some embodiments, the lectin comprises an amino sequence that has about 90 percent similarity or more to the amino acid sequence of SEQ ID NO:1, such as about 91 percent similarity, about 92 percent similarity, about 93 percent similarity, about 94 percent similarity, about 95 percent similarity, about 96 percent similarity, about 97 percent similarity, about 98 percent similarity, or about 99 percent similarity to the amino acid sequence of SEQ ID NO:1.

In some embodiments, the subject is infected by SARS-Cov2 virus, and the method treats, ameliorates, and/or prevents the infection by the SARS-Cov2 virus by limiting the ability of the SARS-Cov2 virus to infect an uninfected cell in the subject.

In some embodiments, the subject is at risk of being infected by SARS-Cov2 virus, and the method prevents the infection by the SARS-Cov2 virus by limiting the ability of the SARS-Cov2 virus to start infect a cell in the subject.

In some embodiments, the subject is a mammal. In some embodiments, the subject is a human.

Method of Treating, Ameliorating and/or Preventing Viral Infection

As described elsewhere herein, the study as described in the specification (also referred to as "the present study"), using Maacki amurensis seed lectin (MASL) and HSC-2 cell line as illustrative non-limiting examples, demonstrates that lectins are able to decrease the expressions of angiotensin-converting enzyme 2 (ACE2) and glycosylases responsible for sialic acid modification of ACE2, and decrease the expression of furin.

SARS-Cov2 virus, the causative agent of COVID-19, interacts with the ACE2, as well as the sialic acid residues on ACE2, via the spike protein of the SARS-Cov2 virus. The attachment of the virus to the host cell is required for the virus to enter and infect the host cell. Furin cleaves a polybasic sequence to unlink the S1 and S2 domains in the SARS-Cov2 spike protein, which promotes virial cell entry. Therefore, lectins are able to inhibit both the attachment and entry of the SARS-Cov2 virus.

Since attachment and entry of SARS-Cov2 virus are required for the initial infection by the virus, lectins can prevent a SARS-Cov2 virus infection in a subject. Since attachment and entry of SARS-Cov2 virus are also required for the propagation of the virus, lectins are expected to treat and/or ameliorate and/or prevent a SARS-Cov2 virus infection in a subject, as well.

The present study, using the illustrative non-limiting examples, further demonstrates that lectins can decrease the expression of A disintegrin and metalloprotease 17 (ADAM17), nuclear factor kappa-light-chain-enhancer of activated B cells (NFκB), signal transducer and activator of transcription 3 (STAT3), TNF superfamily member 10 (TNF SF10), toll-like receptor 3 (TLR3) and toll-like receptor 4 (TLR4), and increase the expression of heme oxygenase 1 (HMOX1) and interleukin 36 receptor antagonist (IL36RN).

ADAM17, NFκB, STAT3, TNFSF10, TLR3 and TLR 4 are inflammatory mediators involved in the upregulation of the cytokine IL6. All these proteins, especially IL6, have been linked to the "cytokine storm" caused by COVID-19, which causes ARDS mediated deaths. National Institutes of Health (NIH) has recommended using monoclonal antibody tocilizumab that blocks IL6 receptor to treat certain COVID-19 patients (NIH, "COVID-19 Treatment Guidelines," updated on Apr. 21, 2021). HMOX1 and IL36RN, on the other hand, inhibit inflammation. IL6, as well as some of the inflammatory mediators, has been liked to cytokine storm and ARDS of other viral disease such as SARS (caused by SARS-CoV infection), MERS (caused by MERS-CoV infection), or flu (caused by influenza virus).

Since lectins downregulates inflammatory mediators involved in the "cytokine storm" caused by viruses, and upregulates inhibitors of inflammation, lectins are expected to treat and/or ameliorate a viral infection in a subject.

Accordingly, in some aspects, the present invention is directed to a method of treating, ameliorating, and/or preventing a viral infection in a subject in need thereof. The method includes administering to the subject a pharmaceutical composition comprising at least one pharmaceutically acceptable carrier and a therapeutically effective amount of a lectin. Pharmaceutically acceptable carriers are known in the art and/or described elsewhere herein.

In some embodiments, the lectin is a Maacki amurensis seed lectin (MASL). In some embodiments, the MASL comprises the amino acid sequence of SEQ ID NO:1, or a biologically active fragment thereof. In some embodiments, the lectin comprises an amino sequence that has about 90 percent similarity or more to the amino acid sequence of SEQ ID NO:1, such as about 91 percent similarity, about 92 percent similarity, about 93 percent similarity, about 94 percent similarity, about 95 percent similarity, about 96 percent similarity, about 97 percent similarity, about 98 percent similarity, or about 99 percent similarity to the amino acid sequence of SEQ ID NO:1.

In some embodiments, the viral infection involves an interaction between a viral surface protein and sialic acid residue on a viral receptor protein on a cell surface of the subject. In some embodiments, the viral receptor protein is angiotensin converting enzyme 2 (ACE2).

In some embodiments, the viral infection causes an inflammatory condition. In some embodiments, the viral infection causes cytokine storm or acute respiratory distress syndrome (ARDS).

In some embodiments, the viral infection is a SARS-CoV infection, a MERS-CoV infection, a SARS-CoV-2 infection, an influenza virus infection, or combinations thereof. In some embodiments, the viral infection is a SARS-CoV-2 infection.

In some embodiments, the viral infection is a SARS-CoV-2 infection, and the method of treating, ameliorating and/or preventing a viral infection further includes administering to the subject a therapeutically effective amount of a second agent believed to be effective in treating the SARS-CoV-2 infection.

In some embodiments, the second agent includes an antiviral agent, such as remdesivir, favipiravir, ivermectin, or the like; an anti-SARS-CoV-2 antibody, such as bamlanivimab, etesevimab, casirivimab, imdevimab, sotrovimab, or the like; an immunomodulator, such as baricitinib, dexamethasone, tocilizumab, or the like. Examples of second agents believed to be effective in treating the SARS-CoV-2 infection are also detailed in, for example, "COVID-19 Treatment Guidelines" published by the National Institute of Health (NIH), the entirety of which is hereby incorporated herein by reference. In some embodiment, the second agent is administered before, after, or at the same time the lectin is administered.

In some embodiments, the subject is a mammal. In some embodiments, the subject is a human.

Method of Treating, Ameliorating, and/or Preventing Inflammation

The present study, using *Maackia amurensis* seed lectin (MASL) and HSC-2 cells as illustrative non-limiting examples, demonstrates that lectins are able to decrease the expression of A disintegrin and metalloprotease 17 (ADAM17), nuclear factor kappa-light-chain-enhancer of activated B cells (NFκB), signal transducer and activator of transcription 3 (STAT3), TNF superfamily member 10 (TNFSF10), toll-like receptor 3 (TLR3) and toll-like receptor 4 (TLR4), and increase the expression of heme oxygenase 1 (HMOX1) and interleukin 36 receptor antagonist (IL36RN).

ADAM17, NFκB, STAT3, TNF SF10, TLR3 and TLR 4 are inflammatory mediators involved in the upregulation of the cytokine IL6. HMOX1 and IL36RN, on the other hand, inhibit inflammation.

Therefore, in some aspects, the present invention is directed to a method of decreasing inflammation in a subject. The method includes administering to the subject a pharmaceutical composition comprising at least one pharmaceutically acceptable carrier and a therapeutically effective amount of a lectin. Pharmaceutically acceptable carriers are known in the art and/or described elsewhere herein.

In some embodiments, the lectin is a Maacki amurensis seed lectin (MASL). In some embodiments, the MASL comprises the amino acid sequence of SEQ ID NO:1, or a biologically active fragment thereof. In some embodiments, the lectin comprises an amino sequence that has about 90 percent similarity or more to the amino acid sequence of SEQ ID NO:1, such as about 91 percent similarity, about 92 percent similarity, about 93 percent similarity, about 94 percent similarity, about 95 percent similarity, about 96 percent similarity, about 97 percent similarity, about 98 percent similarity, or about 99 percent similarity to the amino acid sequence of SEQ ID NO:1.

In some embodiments, the inflammation is caused by overexpression of ADAM17, NFκB, STAT3, TNFSF10, TLR3, TLR 4, IL6, or combinations thereof.

In some embodiments, the inflammation is caused by a viral infection in the subject. In some embodiments, the inflammation is caused by a SARS-CoV infection, a MERS-CoV infection, a SARS-CoV-2 infection, an influenza virus infection, or combinations thereof, in the subject. In some embodiments, the inflammation is caused by a SARS-CoV-2 infection. In some embodiments, the inflammation includes a cytokine storm or acute respiratory distress syndrome (ARDS). In some embodiments, the cytokine storm or the acute respiratory distress syndrome (ARDS) is caused by a viral infection.

In some embodiments, the subject is a mammal. In some embodiments, the subject is a human.

Combination Therapies

In some embodiments, the subject is further administered at least one additional agent that treats, ameliorates, and/or prevents a disease and/or disorder contemplated herein. In other embodiments, the compound described herein and the at least one additional agent are co-administered to the subject. In some embodiments, the at least one additional agent are co-administered is administered before, after, or at the same time the compound described herein is administered. In yet other embodiments, the compound and the at least one additional agent are co-formulated.

The compounds contemplated within the disclosure are intended to be useful in combination with one or more additional compounds. These additional compounds may comprise compounds of the present disclosure and/or at least one additional agent for treating neurodegenerative conditions, and/or at least one additional agent that treats one or more diseases or disorders contemplated herein.

A synergistic effect may be calculated, for example, using suitable methods such as, for example, the Sigmoid-$E_{max}$ equation (Holford & Scheiner, 1981, Clin. Pharmacokinet. 6:429-453), the equation of Loewe additivity (Loewe & Muischnek, 1926, Arch. Exp. Pathol Pharmacol. 114:313-326) and the median-effect equation (Chou & Talalay, 1984, Adv. Enzyme Regul. 22:27-55). Each equation referred to above may be applied to experimental data to generate a corresponding graph to aid in assessing the effects of the drug combination. The corresponding graphs associated with the equations referred to above are the concentration-effect curve, isobologram curve and combination index curve, respectively.

Administration/Dosage/Formulations

Routes of administration of any of the compositions of the invention include oral, nasal, rectal, intravaginal, parenteral (e.g., IM, IV and SC), buccal, sublingual or topical. The regimen of administration may affect what constitutes an effective amount. The therapeutic formulations may be administered to the subject either prior to or after the onset of a viral infection. Further, several divided dosages, as well as staggered dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation.

Administration of the compositions of the present invention to a subject, preferably a mammal, more preferably a human, may be carried out using known procedures, at dosages and for periods of time effective to treat a viral infection in the subject. An effective amount of the therapeutic compound necessary to achieve a therapeutic effect may vary according to factors such as the state of the disease or disorder in the subject; the age, sex, and weight of the subject; and the ability of the therapeutic compound to treat a viral infection in the subject. Dosage regimens may be adjusted to provide the optimum therapeutic response. For example, several divided doses may be administered daily or the dose may be proportionally reduced as indicated by the exigencies of the therapeutic situation. A non-limiting example of an effective dose range for a therapeutic compound useful within the invention is from about 1 and 5,000 mg/kg of body weight/per day. One of ordinary skill in the art would be able to study the relevant factors and make the determination regarding the effective amount of the therapeutic compound without undue experimentation.

Actual dosage levels of the active ingredients in the pharmaceutical compositions of this invention may be varied so as to obtain an amount of the active ingredient that is effective to achieve the desired therapeutic response for a particular subject, composition, and mode of administration, without being toxic to the subject.

In particular, the selected dosage level depends upon a variety of factors, including the activity of the particular compound employed, the time of administration, the rate of excretion of the compound, the duration of the treatment, other drugs, compounds or materials used in combination with the compound, the age, sex, weight, condition, general health and prior medical history of the subject being treated, and like factors well, known in the medical arts.

A medical doctor, e.g., physician or veterinarian, having ordinary skill in the art may readily determine and prescribe the effective amount of the pharmaceutical composition required. For example, the physician or veterinarian may start doses of the compounds useful within the invention employed in the pharmaceutical composition at levels lower than that required in order to achieve the desired therapeutic effect and gradually increase the dosage until the desired effect is achieved.

In one embodiment, it is especially advantageous to formulate the compound in dosage unit form for ease of administration and uniformity of dosage. Dosage unit form as used herein refers to physically discrete units suited as unitary dosages for the subjects to be treated; each unit containing a predetermined quantity of therapeutic compound calculated to produce the desired therapeutic effect in association with the required pharmaceutical vehicle. The dosage unit forms of the invention are dictated by and directly dependent on the unique characteristics of the therapeutic compound and the particular therapeutic effect to be achieved, and the limitations inherent in the art of compounding/formulating such a therapeutic compound for the treatment of an COVID-19 infection in a subject.

In one embodiment, the compositions of the invention are formulated using one or more pharmaceutically acceptable excipients or carriers. In one embodiment, the pharmaceutical compositions of the invention comprise a therapeutically effective amount of a compound useful within the invention and a pharmaceutically acceptable carrier.

The language "pharmaceutically acceptable carrier" includes a pharmaceutically acceptable salt, pharmaceutically acceptable material, composition or carrier, such as a liquid or solid filler, diluent, excipient, solvent or encapsulating material, involved in carrying or transporting a compound(s) of the present invention within or to the subject such that it may perform its intended function. Typically, such compounds are carried or transported from one organ, or portion of the body, to another organ, or portion of the body. Each salt or carrier must be "acceptable" in the sense of being compatible with the other ingredients of the formulation, and not injurious to the subject.

The carrier may be a solvent or dispersion medium containing, for example, water, ethanol, polyol (for example, glycerol, propylene glycol, and liquid polyethylene glycol, and the like), suitable mixtures thereof, and vegetable oils. The proper fluidity may be maintained, for example, by the use of a coating such as lecithin, by the maintenance of the required particle size in the case of dispersion and by the use of surfactants. Prevention of the action of microorganisms may be achieved by various antibacterial and antifungal agents, for example, parabens, chlorobutanol, phenol, ascorbic acid, thimerosal, and the like. In many cases, it is preferable to include isotonic agents, for example, sugars, sodium chloride, or polyalcohols such as mannitol and sorbitol, in the composition. Prolonged absorption of the injectable compositions may be brought about by including in the composition an agent which delays absorption, for example, aluminum monostearate or gelatin. In one embodiment, the pharmaceutically acceptable carrier is not DMSO alone.

In one embodiment, the compositions of the invention are administered to the subject in dosages that range from one to five times per day or more. In another embodiment, the compositions of the invention are administered to the subject in range of dosages that include, but are not limited to, once every day, every two, days, every three days to once a week, and once every two weeks. It is readily apparent to one skilled in the art that the frequency of administration of the various combination compositions of the invention varies from individual to individual depending on many factors including, but not limited to, age, disease or disorder to be treated, gender, overall health, and other factors. Thus, the invention should not be construed to be limited to any particular dosage regime and the precise dosage and composition to be administered to any subject are determined by the attending physical taking all other factors about the subject into account.

Compounds useful within the invention for administration may be in the range of from about 1 mg to about 10,000 mg, about 20 mg to about 9,500 mg, about 40 mg to about 9,000 mg, about 75 mg to about 8,500 mg, about 150 mg to about 7,500 mg, about 200 mg to about 7,000 mg, about 3050 mg to about 6,000 mg, about 500 mg to about 5,000 mg, about 750 mg to about 4,000 mg, about 1 mg to about 3,000 mg, about 10 mg to about 2,500 mg, about 20 mg to about 2,000 mg, about 25 mg to about 1,500 mg, about 50 mg to about 1,000 mg, about 75 mg to about 900 mg, about 100 mg to about 800 mg, about 250 mg to about 750 mg, about 300 mg to about 600 mg, about 400 mg to about 500 mg, and any and all whole or partial increments therebetween.

In some embodiments, the dose of a compound useful within the invention is from about 1 mg and about 2,500 mg. In some embodiments, a dose of a compound useful within the invention used in compositions described herein is less than about 10,000 mg, or less than about 8,000 mg, or less than about 6,000 mg, or less than about 5,000 mg, or less than about 3,000 mg, or less than about 2,000 mg, or less than about 1,000 mg, or less than about 500 mg, or less than about 200 mg, or less than about 50 mg. Similarly, in some embodiments, a dose of a second compound (i.e., an COVID-19 antiviral) as described herein is less than about 1,000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments therebetween.

In one embodiment, the present invention is directed to a packaged pharmaceutical composition comprising a container holding a therapeutically effective amount of a compound useful within the invention, alone or in combination with a second pharmaceutical agent; and instructions for using the compound to treat, prevent, or reduce one or more symptoms of an COVID-19 infection in a subject.

Granulating techniques are well known in the pharmaceutical art for modifying starting powders or other particulate materials of an active ingredient. The powders are typically mixed with a binder material into larger permanent free-flowing agglomerates or granules referred to as a "granulation." For example, solvent-using "wet" granulation processes are generally characterized in that the powders are combined with a binder material and moistened with water or an organic solvent under conditions resulting in the formation of a wet granulated mass from which the solvent must then be evaporated.

Melt granulation generally consists in the use of materials that are solid or semi-solid at room temperature (i.e. having a relatively low softening or melting point range) to promote granulation of powdered or other materials, essentially in the absence of added water or other liquid solvents. The low melting solids, when heated to a temperature in the melting point range, liquefy to act as a binder or granulating medium. The liquefied solid spreads itself over the surface of powdered materials with which it is contacted, and on cooling, forms a solid granulated mass in which the initial materials are bound together. The resulting melt granulation may then be provided to a tablet press or be encapsulated for preparing the oral dosage form. Melt granulation improves the dissolution rate and bioavailability of an active (i.e. drug) by forming a solid dispersion or solid solution.

U.S. Pat. No. 5,169,645 discloses directly compressible wax-containing granules having improved flow properties. The granules are obtained when waxes are admixed in the melt with certain flow improving additives, followed by cooling and granulation of the admixture. In certain embodiments, only the wax itself melts in the melt combination of the wax(es) and additives(s), and in other cases both the wax(es) and the additives(s) will melt.

The present invention also includes a multi-layer tablet comprising a layer providing for the delayed release of one or more compounds useful within the invention, and a further layer providing for the immediate release of a medication for COVID-19 infection. Using a wax/pH-sensitive polymer mix, a gastric insoluble composition may be obtained in which the active ingredient is entrapped, ensuring its delayed release.

Formulations may be employed in admixtures with conventional excipients, i.e., pharmaceutically acceptable organic or inorganic carrier substances suitable for oral, parenteral, nasal, intravenous, subcutaneous, enteral, or any other suitable mode of administration, known to the art. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They may also be combined where desired with other active agents, e.g., other analgesic agents. For oral application, particularly suitable are tablets, dragees, liquids, drops, suppositories, or capsules, caplets and gelcaps. The compositions intended for oral use may be prepared according to any method known in the art and such compositions may contain one or more agents selected from the group consisting of inert, non-toxic pharmaceutically excipients that are suitable for the manufacture of tablets. Such excipients include, for example an inert diluent such as lactose; granulating and disintegrating agents such as cornstarch; binding agents such as starch; and lubricating agents such as magnesium stearate. The tablets may be uncoated or they may be coated by known techniques for elegance or to delay the release of the active ingredients. Formulations for oral use may also be presented as hard gelatin capsules wherein the active ingredient is mixed with an inert diluent.

The term "container" includes any receptacle for holding the pharmaceutical composition. For example, in one embodiment, the container is the packaging that contains the pharmaceutical composition. In other embodiments, the container is not the packaging that contains the pharmaceutical composition, i.e., the container is a receptacle, such as a box or vial that contains the packaged pharmaceutical composition or unpackaged pharmaceutical composition and the instructions for use of the pharmaceutical composition. Moreover, packaging techniques are well known in the art. It should be understood that the instructions for use of the pharmaceutical composition may be contained on the packaging containing the pharmaceutical composition, and as such the instructions form an increased functional relationship to the packaged product. However, it should be understood that the instructions may contain information pertaining to the compound's ability to perform its intended function, e.g., treating, preventing, or reducing an COVID-19 infection in a subject.

The compounds for use in the invention may be formulated for administration by any suitable route, such as for oral or parenteral, for example, transdermal, transmucosal (e.g., sublingual, lingual, (trans)buccal, (trans)urethral, vaginal (e.g., trans- and perivaginally), (intra)nasal and (trans) rectal), intravesical, intrapulmonary, intraduodenal, intragastrical, intrathecal, subcutaneous, intramuscular, intradermal, intra-arterial, intravenous, intrabronchial, inhalation, and topical administration.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present invention are not limited to the particular formulations and compositions that are described herein.

Oral Administration

For oral administration, the compositions of the invention may be in the form of tablets or capsules prepared by conventional means with pharmaceutically acceptable excipients such as binding agents (e.g., polyvinylpyrrolidone, hydroxypropylcellulose or hydroxypropylmethylcellulose); fillers (e.g., cornstarch, lactose, microcrystalline cellulose or calcium phosphate); lubricants (e.g., magnesium stearate, talc, or silica); disintegrates (e.g., sodium starch glycollate); or wetting agents (e.g., sodium lauryl sulphate). If desired, the tablets may be coated using suitable methods and coating materials such as OPADRY™ film coating systems available from Colorcon, West Point, Pa. (e.g., OPADRY™ OY Type, OYC Type, Organic Enteric OY-P Type, Aqueous Enteric OY-A Type, OY-PM Type and OPADRYυ White, 32K18400). Liquid preparation for oral administration may be in the form of solutions, syrups or suspensions. The liquid preparations may be prepared by conventional means with pharmaceutically acceptable additives such as suspending agents (e.g., sorbitol syrup, methyl cellulose or hydrogenated edible fats); emulsifying agent (e.g., lecithin or acacia); non-aqueous vehicles (e.g., almond oil, oily esters or ethyl alcohol); and preservatives (e.g., methyl or propyl p-hydroxy benzoates or sorbic acid).

Parenteral Administration

For parenteral administration, the compositions of the invention may be formulated for injection or infusion, for example, intravenous, intramuscular or subcutaneous injection or infusion, or for administration in a bolus dose and/or continuous infusion. Suspensions, solutions or emulsions in an oily or aqueous vehicle, optionally containing other formulatory agents such as suspending, stabilizing and/or dispersing agents may be used.

Additional Administration Forms

Additional dosage forms of this invention include dosage forms as described in U.S. Pat. Nos. 6,340,475, 6,488,962, 6,451,808, 5,972,389, 5,582,837, and 5,007,790. Additional dosage forms of this invention also include dosage forms as described in U.S. Patent Applications Nos. 2003/0147952, 2003/0104062, 2003/0104053, 2003/0044466, 2003/0039688, and 2002/0051820. Additional dosage forms of this invention also include dosage forms as described in PCT Applications Nos. WO 03/35041, WO 03/35040, WO 03/35029, WO 03/35177, WO 03/35039, WO 02/96404, WO 02/32416, WO 01/97783, WO 01/56544, WO 01/32217, WO 98/55107, WO 98/11879, WO 97/47285, WO 93/18755, and WO 90/11757.

Controlled Release Formulations and Drug Delivery Systems

In certain embodiments, the formulations of the present invention may be, but are not limited to, short-term, rapid-offset, as well as controlled, for example, sustained release, delayed release and pulsatile release formulations.

The term sustained release is used in its conventional sense to refer to a drug formulation that provides for gradual release of a drug over an extended period of time, and that may, although not necessarily, result in substantially constant blood levels of a drug over an extended time period. The period of time may be as long as a month or more and should be a release which is longer that the same amount of agent administered in bolus form.

For sustained release, the compounds may be formulated with a suitable polymer or hydrophobic material which provides sustained release properties to the compounds. As such, the compounds for use the method of the invention may be administered in the form of microparticles, for example, by injection or in the form of wafers or discs by implantation.

In some non-limiting embodiments, the compounds useful within the invention are administered to a subject, alone or in combination with another pharmaceutical agent, using a sustained release formulation.

The term delayed release is used herein in its conventional sense to refer to a drug formulation that provides for an initial release of the drug after some delay following drug administration and that may, although not necessarily, include a delay of from about 10 minutes up to about 12 hours.

The term pulsatile release is used herein in its conventional sense to refer to a drug formulation that provides release of the drug in such a way as to produce pulsed plasma profiles of the drug after drug administration.

The term immediate release is used in its conventional sense to refer to a drug formulation that provides for release of the drug immediately after drug administration.

As used herein, short-term refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes and any or all whole or partial increments thereof after drug administration after drug administration.

As used herein, rapid-offset refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes, and any and all whole or partial increments thereof after drug administration.

Dosing

The therapeutically effective amount or dose of a compound of the present invention will depend on the age, sex and weight of the subject, the current medical condition of the subject and the nature of the infection by an COVID-19 being treated. The skilled artisan will be able to determine appropriate dosages depending on these and other factors.

A suitable dose of a compound of the present invention may be in the range of from about 0.01 mg to about 5,000 mg per day, such as from about 0.1 mg to about 1,000 mg, for example, from about 1 mg to about 500 mg, such as about 5 mg to about 250 mg per day. The dose may be administered in a single dosage or in multiple dosages, for example from 1 to 4 or more times per day. When multiple dosages are used, the amount of each dosage may be the same or different. For example, a dose of 1 mg per day may be administered as two 0.5 mg doses, with about a 12-hour interval between doses.

It is understood that the amount of compound dosed per day may be administered, in non-limiting examples, every day, every other day, every 2 days, every 3 days, every 4 days, or every 5 days.

The compounds for use in the method of the invention may be formulated in unit dosage form. The term "unit dosage form" refers to physically discrete units suitable as unitary dosage for subjects undergoing treatment, with each unit containing a predetermined quantity of active material calculated to produce the desired therapeutic effect, optionally in association with a suitable pharmaceutical carrier. The unit dosage form may be for a single daily dose or one of multiple daily doses (e.g., about 1 to 4 or more times per day). When multiple daily doses are used, the unit dosage form may be the same or different for each dose.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

EXAMPLES

Various embodiments of the present application can be better understood by reference to the following Examples which are offered by way of illustration. The scope of the present application is not limited to the Examples given herein.

Example 1: Pilot Study

Pilot data indicates that MASL targets sialic acid modified receptors, decreases ACE2 and associated glycosylase expression, and inhibits SARS-CoV-2 spike protein binding on oral squamous cells (OSCs). MASL can be administered orally with no reported side effects, and decreases the expression of inflammatory cytokines associated with COVID-19 infections. GMP MASL have been produced, and IRB and USFDA approval for a Phase I study of its effects on oral cancer patients have been obtained.

In certain embodiments, MASL decreases ACE2 expression and targets ACE2 on oral epithelial cells to combat COVID-19 infection and related inflammation.

The supporting data indicate that: (1) SARS-CoV-2 spike protein and ACE2 are glycosylated with sialic acid moieties; (2) MASL targets sialic acid modified receptors on OSCs; and (3) MASL inhibits SARS-CoV-2 spike protein binding to OSCs. How MASL inhibits SARS-CoV-2 infection of OSCs alone and in combination with other agents in vitro and in a Phase 1 clinical trial in COVID-19 patients were determined.

The supporting data indicate that: (1) MASL reduces cytokine expression and inflammation in cell culture and in vivo; and (2) MASL inhibits TLR, STAT3, IL6, and NFκB signaling in OSCs. The effects of MASL on these inflammatory signaling pathways were analyzed to determine how it can be used to reduce inflammation in COVID-19 patients.

This project utilized MASL as a nontoxic IND ready compound to inhibit ACE2 expression, SARS-CoV-2-infection, and COVID-19 inflammation by way of the oral mucosa.

SARS-CoV-2 is the latest member of 7 coronaviruses that infect humans. Four members (HKU1, NL63, OC43, and 229E) cause relatively mild symptoms, while the other 3 (SARS-CoV, MERSCoV, and SARS-CoV-2) can cause severe disease. SARS-CoV-2 contains a positive sense single stranded RNA genome of about 30 kb encoding RNA polymerases, proteases, and structural proteins including the spike (S), envelope (E), membrane (M), and nucleocapsid (N) (FIG. 1).

The SARS-CoV-2 spike protein targets the angiotensin converting enzyme 2 (ACE2) receptor on host cells. This interaction is mediated by a receptor binding domain (RBD) in the S1 portion of the spike protein that recognizes the human ACE2 extracellular domain. The SARS-CoV-2 RBD has a high affinity for human ACE2, but can also target other species including ferrets and cats.

Figure 2:
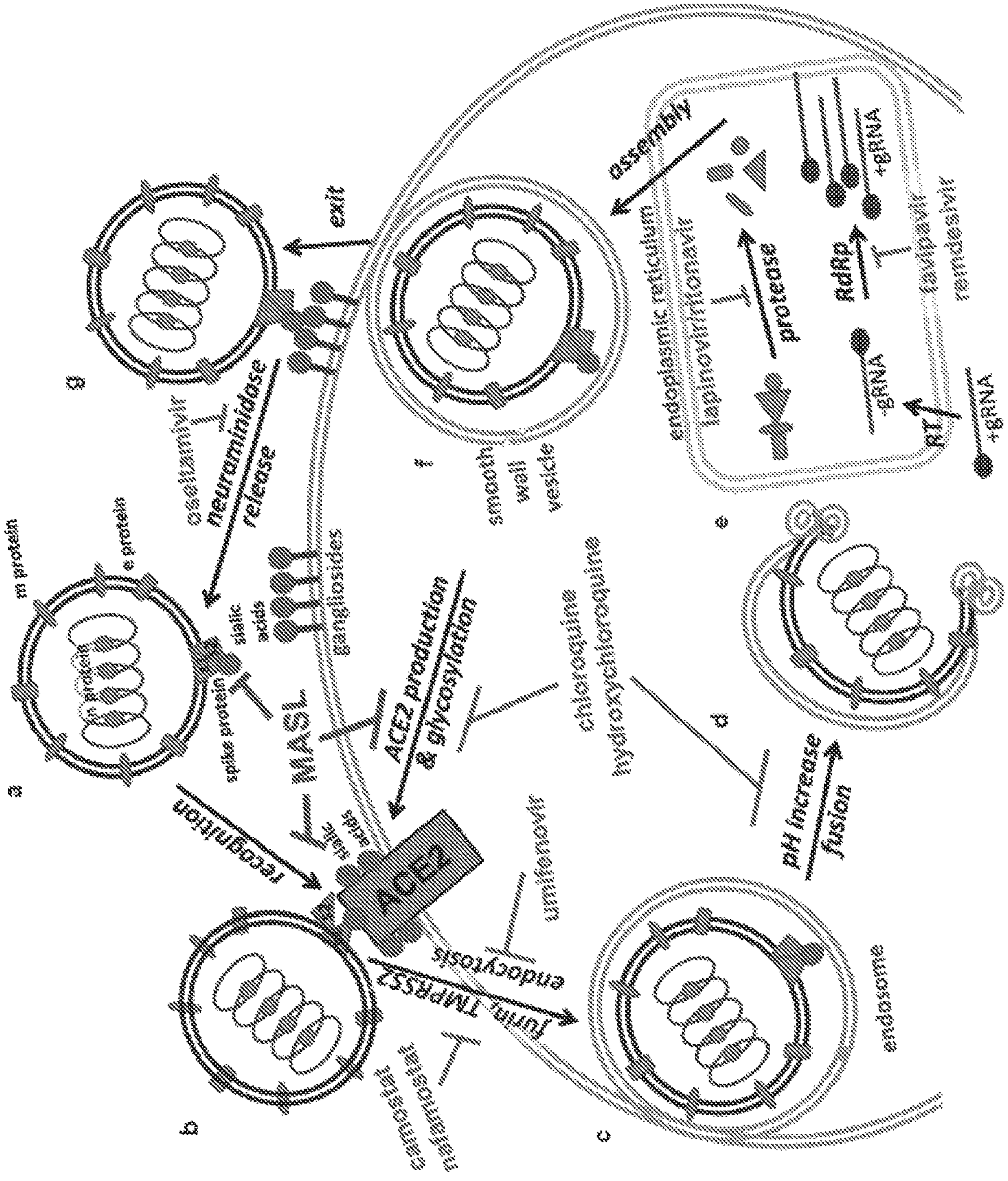
FIG. 2 shows SARS-CoV-2 host interactions and therapies. Panel A: SARS spike protein targets the ACE2 receptor on host cells. Panels B-C: Furin and TMPRSS2 separate S1 and S2 domains to promote endocytosis, which can be inhibited by TMPRSS2 (e.g. camostat, nafamostat) and endocytosis (umifenovir) blockers. Panel D: internalized endosome and virus membranes fuse to release the viral genome for cytoplasmic replication and assembly, which can be inhibited by chloroquine. Panel E: after intracellular release, viral gRNA, polymerases, and proteases produce new virus particles, which can be inhibited by protease (lopinavir/ritonavir) and RdRP (remdesivir, favipiravir) blockers. Panel F: replicated SARS proteins and gRNA are packaged into virions in a smooth wall vesicle from the endoplasmic reticulum which exit the cell by exocytosis, but are held in place at the plasma membrane by interactions with extracellular sialic acid residues. Panel G: neuraminidase cleaves these sialic acids to release newly produced viruses, which can be inhibited by neuraminidase blockers (oseltamivir).

The SARS-CoV-2 spike and host ACE2 proteins are both heavily glycosylated with sialic acids needed for viral infection. N-acetylneuraminic acid (Neu5Ac, NANA) is the predominant human sialic acid; humans do not produce N-glycoylneuraminic acid (Neu5Gc) since loss of the cytidine monophospho-N-acetylneuraminic acid hydroxylase (CMAH) gene during evolution. The term "sialic acid" as used herein refers to Neu5Ac (NANA) and other related moieties found on glycoproteins, as well as glycolipids including gangliosides expressed by epithelial cells and neurons. Sialic acids act as viral receptors, and are critical for host-viral interactions. This was noted earlier for influenza virus, and now SARS-CoV-2. In general, glycosylation events can be N-linked (to Asn or Arg residues) or O-linked (to Ser, Thr, or Tyr) to proteins. The SARS-CoV-2 spike protein has at least 22 N-linked glycosylation sequons per protomer, and about 15% of these glycans contain at least one sialic acid residue. The human ACE2 receptor contains 7 N-linked and 3 O-linked glycans, and they all contain sialic acid residues. Interestingly, chloroquine and its more active prodrug hydroxychloroquine inhibit ACE2 posttranslational modifications and bind to sialic acids, which decreases binding of the SARS spike protein to its host receptors (FIG. 2).

Transmembrane protease serine 2 (TMPRSS2) and furin cleave a polybasic sequence to unlink the S1 and S2 domains in the SARS spike protein to promote viral entry. After binding to the cell, furin and TMPRSS2 act coordinately to cleave the spike protein at the cell membrane. The S1 domain maintains affinity for Ace2, while the S2 domain mediates membrane fusion and endocytosis. TMPRSS2 inhibitors (e.g. camostat, nafamostat) and endocytosis blockers (umifenovir) can inhibit this process to prevent viral entry as shown in FIG. 2, Panels A-B.

After internalization, endosome and virus membranes fuse to release the viral genome for cytoplasmic replication and assembly. This process results from intracellular endosomal pH elevation and activity of the host cysteine protease cathepsin. Chloroquine can inhibit this process in addition to inhibiting ACE2 receptor recognition described above and shown in FIG. 2, Panels C-D.

After intracellular release, 2 open reading frames (ORFS) in the viral gRNA are translated into a polypeptide precursor protein that is cleaved to produce viral proteins. These proteins include a reverse transcriptase that produces antisense viral RNA intermediates which serve as templates for viral RNA-dependent RNA polymerase (RdRP) that synthesizes new gRNA. This process can be inhibited by viral protease blockers (lopinavir/ritonavir) and nucleotide analog RdRP blockers (remdesivir, favipiravir) to suppress viral proliferation as shown in FIG. 2, Panel E.

Replicated SARS proteins and gRNA are packaged into virions that are encapsulated in a smooth wall vesicle from the endoplasmic reticulum. These virions exit the cell by exocytosis, but are held in place at the plasma membrane by interactions with extracellular sialic acid residues. Neuraminidase cleaves these sialic acids to release newly produced viruses. Neuraminidase blockers inhibit this reaction to decrease viral release and subsequent expansion. Although this process is not as clearly demonstrated for SARS as it is for influenza, neuraminidase blockers (oseltamivir) are being examined as potential COVID-19 treatments as shown in FIG. 2, Panel G.

New COVID-19 treatment options are clearly needed. COVID-19 therapy options are currently focused on ACE2 modification (chloroquine), TMPRSS2 (e.g. camostat, nafamostat), endocytosis (umifenovir), endosome release (chloroquine, hydroxychloroquine), protease (lopinavir/ritonavir), RdRP (remdesivir, favipiravir), and neuraminidase (oseltamivir) blockers. However, these agents offer questionable efficacy and cause side effects from pruritus to liver damage and heart failure. *Maackia amurensis* seed lectin (MASL) is used herein to help ameliorate this crisis.

*Maackia amurensis* seed lectin (MASL) targets sialic acid modified glycoprotein receptors. Lectins recognize specific glycosylation motifs, and can be used as antiviral agents. In particular, MASL has an exceptionally strong affinity for O-linked and N-linked sialic acid modified proteins. MASL targets specific receptors, exemplified by the sialic acid modified receptor podoplanin (PDPN), to inhibit cancer progression and inflammation. Indeed, MASL targets PDPN on oral squamous cells with surprising efficiency and dynamics. The SARS-CoV-2 spike protein presents several sialic acid residues. In addition, the human ACE2 receptor contains at least 13 glycans with sialic acid residues.

Lectins offer significant medicinal value. Toxic lectins (e.g. ricin and viscumin) are extremely rare. In fact, lectins are found in virtually all foods. In addition to carbohydrate modifications, lectin interactions are guided by amino acid residues on their target receptor proteins. Lectins can bind to their receptors with specificity and affinity that rival the specificity of kinase inhibitors (e.g. lapatinib or imatinib) and therapeutic antibodies (e.g. trastuzumab). For example, C-type lectin-like receptor 2 (CLEC-2) targets PDPN with an average dissociation constant ($K_d$) of less than 4 nM. In addition, unlike antibodies, lectins are resistant to gastrointestinal proteolysis, and can be administered orally to treat disease. For example, lectins can block the action of endogenous pro-metastatic lectins (such as galectins or selectins) to inhibit tumor cell growth, and can be used to treat cancer and viral infections. However, most medicinal lectins that have been examined thus far have intrinsically toxic ribosome inhibitory protein (RIP) activity similar to that of ricin. Unlike these other lectins, MASL is not toxic to normal cells.

As described herein, lectins offer the advantage of oral administration. Dietary legumes have been shown to significantly lower the incidence of skin cancer. Digestion of 200 grams of peanuts results in concentrations of up to 200 nM of intact peanut lectin (PNA) in circulating blood. MASL can survive digestion and enter the circulatory system to inhibit tumor progression and arthritic inflammation. Oral administration presents options for treatment with strong advantages over agents such as antibodies that require intravenous administration.

Human safety of MASL has already been demonstrated as a "coincidental" component in traditional medicines. For example, *Maackia amurensis* has been used as a medicinal plant in parts of Asia for several centuries.

COVID-19 causes inflammation leading to severe acute respiratory distress syndrome (ARDS), which kills about 2% of infected individuals. This mortality rate is over times higher than that of the seasonal influenza virus. Inhibiting COVID-19 inflammation should reduce mortality for COVID-19 patients. MASL inhibits inflammatory pathways including STAT3, IL6, and TNF activation that lead to COVID-19 pathologies.

Figure 3:
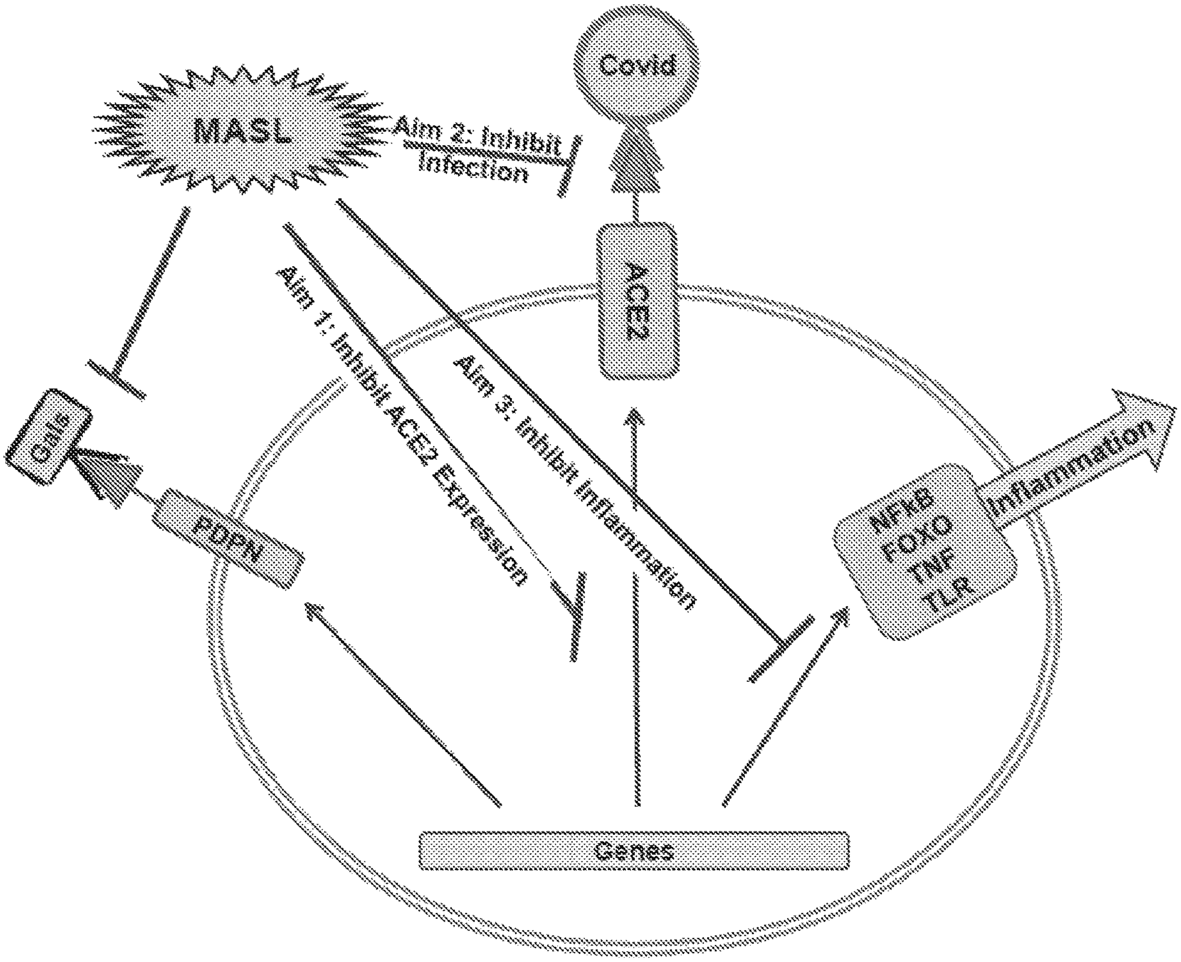
FIG. 3 shows the specific aspects: (1) determine how MASL decreases ACE2 expression in epithelial cells; (2) examine how MASL affects SARS-CoV-2 infection; (3) elucidate the effects of MASL on SARS-CoV-2 associated inflammation.

The pilot data indicate that MASL can decrease ACE2 expression and sialic acid modification, inhibit SARS-CoV-2 infection, and/or decrease COVID-19 related inflammation. The SARS-CoV-2 spike and human ACE2 proteins are both decorated with sialic acid residues that are recognized by MASL. MASL inhibits expression of ACE2, sialic acid glycosylates, and inflammatory cytokines in oral epithelial cells as shown in FIG. 2 and FIG. 3. MASL offers an opportunity to target these cells topically and systemically by oral administration. In certain embodiments, MASL can be used alone or in combination with other agents to help combat the COVID-19 pandemic.

This project introduces a novel approach to simultaneously block key steps of SARS-CoV-2 pathogenesis. This novel approach offers the benefit of using MASL as an orally administrated pleiotropic natural product to combat the COVID-19 pandemic. MASL was developed and purified, and IRB and FDA IND approvals for MASL were obtained which can be rapidly translated for clinical use. The pilot studies indicate that MASL: (1) decreases ACE2 production in human oral squamous cells (OSCs); (2) decreases production of glycosylases needed for ACE2 and spike protein glycosylation; (3) targets sialic modified receptors expressed by epithelial cells including ACE2; (4) prevents SARS-CoV-2 spike protein binding to human OSCs; and (5) inhibits NF-kB signaling and COVID-19 related inflammatory cytokine production in human OSCs.

SARS-CoV-2 targets the ACE2 receptor, which is expressed on cells of the oral mucosa. The ACE2 receptor and viral spike protein both represent sialic acids needed for viral-host interactions. MASL recognizes these glycosylation motifs and target specific receptors to inhibit cancer progression and inflammation and is an effective antiviral agent. The pilot data indicate that MASL also decreases ACE2 expression and glycosylase expression needed for its posttranslational modification in oral squamous cells (OSCs). In certain embodiments, MASL can be used to inhibit SARS-CoV-2 infection and pathologies. As shown in FIG. 3, three (3) specific aims to investigate how MASL affects were proposed: (1) ACE2 expression; (2) SARS-CoV-2 infection, and (3) COVID-19 inflammation.

Example 1-1: MASL Affects ACE2 Expression and Glycosylation

Figure 4A:
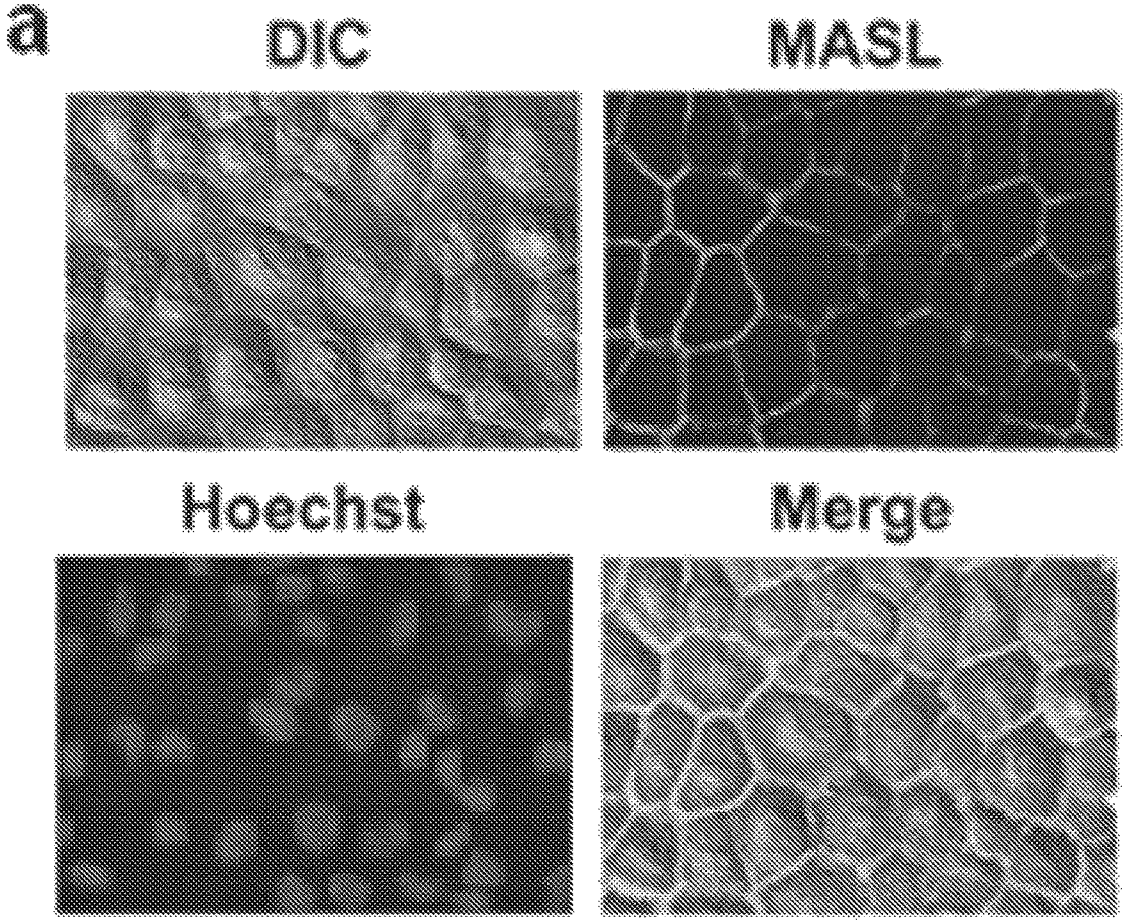
FIGS. 4A-B show MASL dynamically targets PDPN on OSCC cells.
Figure 4B:
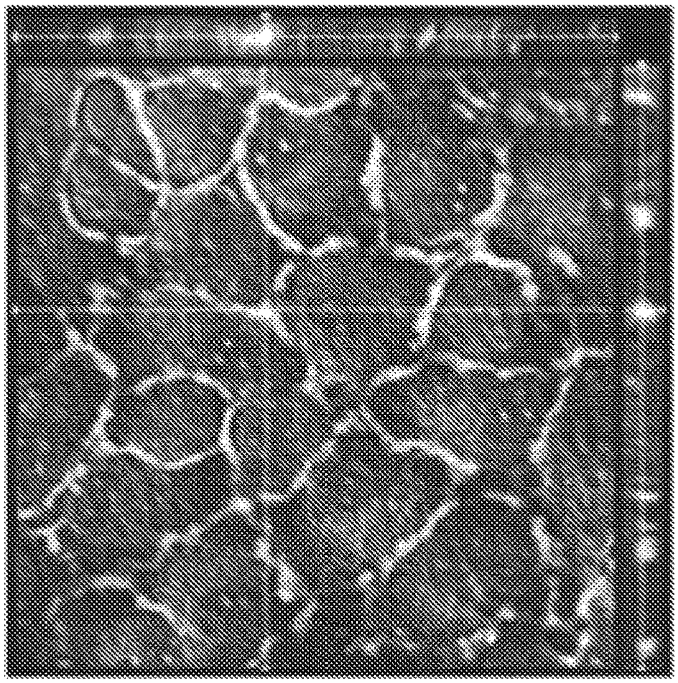
Figure 5:
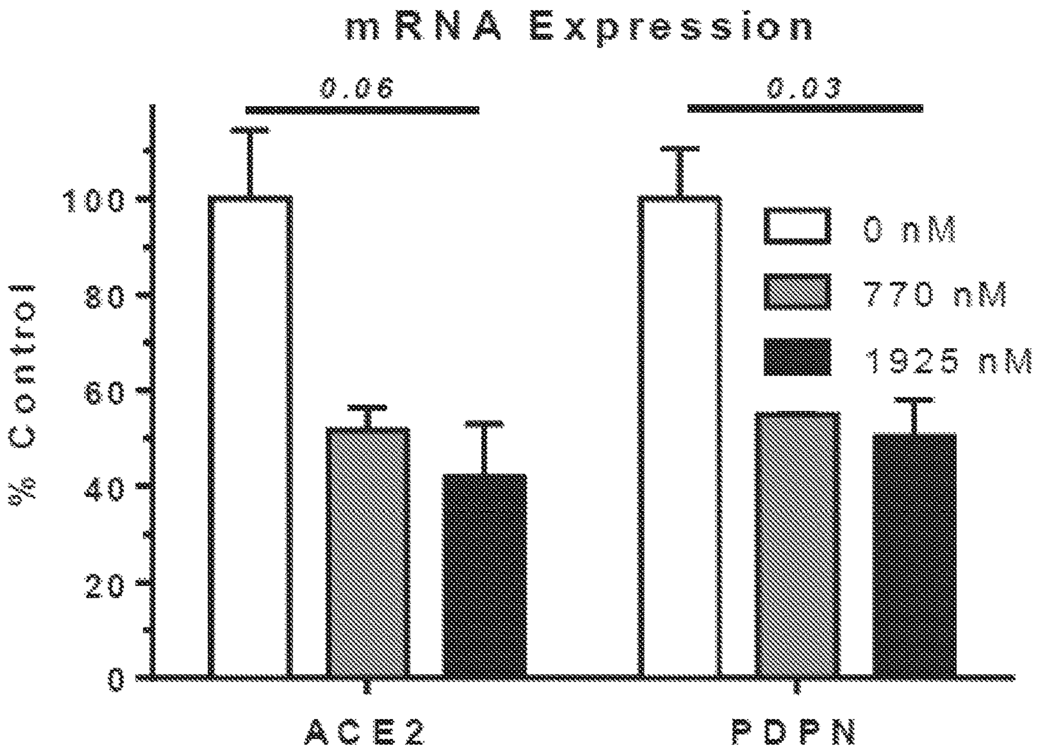
FIG. 5: MASL inhibits ACE2 and PDPN expression. HSC2 cells treated with 0, 770, or 1925 nM MASL for 12 hours were examined by RAN-Seq. Data are shown as a percentage of untreated controls (mean±SEM, n=2) and p values by ANOVA.

The pilot data indicate that MASL decreases ACE2 expression in OSCs. MASL targets the PDPN receptor on human oral squamous cell carcinoma cells within 2 minutes of exposure as shown in FIG. 4. PDPN is a transcellular protein which contains many extracellular sialic residues that are recognized by MASL. In certain embodiments, MASL targets ACE2 and spike protein in a similar way, which is examined in Example 1-2. The main point here is that MASL targets human oral epithelial cells very efficiently. Moreover, MASL decreases ACE2 expression in these cells. MASL decreases ACE2 mRNA levels by nearly 50% and 60% at 770 nM and 1925 nM, respectively, as shown in FIG. 5. Interestingly, MASL also decreases PDPN expression in these cells to a similar extent by nearly 45% and 50% by 770 nM and 1925 nM, respectively (FIG. 5).

The effects of MASL on ACE2 expression were evaluated. Having found that MASL can inhibit ACE2 expression, the present study then investigated the generality and cellular dynamics of this activity. ACE2 mRNA and protein expression in OSCs exposed to 0.5, 1, 2, and 4 μM MASL for 12, 24, 48, and 72 hours were examined by qRT-PCR and Western blotting, respectively. The effects of MASL on cell viability were also examined by Alamar Trypan blue viability assays, and standard cell counting. These data were used to identify optimal concentrations that decrease ACE2 expression without affecting cell viability. ACE2 expression in cells exposed to optimal MASL concentrations and time frames, and then grown without MASL at specific time points were then examined to evaluate the duration of ACE2 suppression. These experiments are used to determine MASL dose response, and minimal concentrations needed to reduce ACE2 expression, as well as recovery rates and durations needed to maintain ACE2 suppression.

Established and primary OCS cells were utilized for this study. HSC2 cells, which are oral squamous cell carcinoma (OSCC) cells obtained from the mouth floor of a 69 year old male oral cancer patient, were used. These cells are HPV negative and well sited as an entry model for this study. A variety of oral epithelial cells obtained from other patients as previously described, as well as up to 50 additional oral epithelial cell lines obtained in the course of a MASL based clinical trial were also used.

Figure 6:
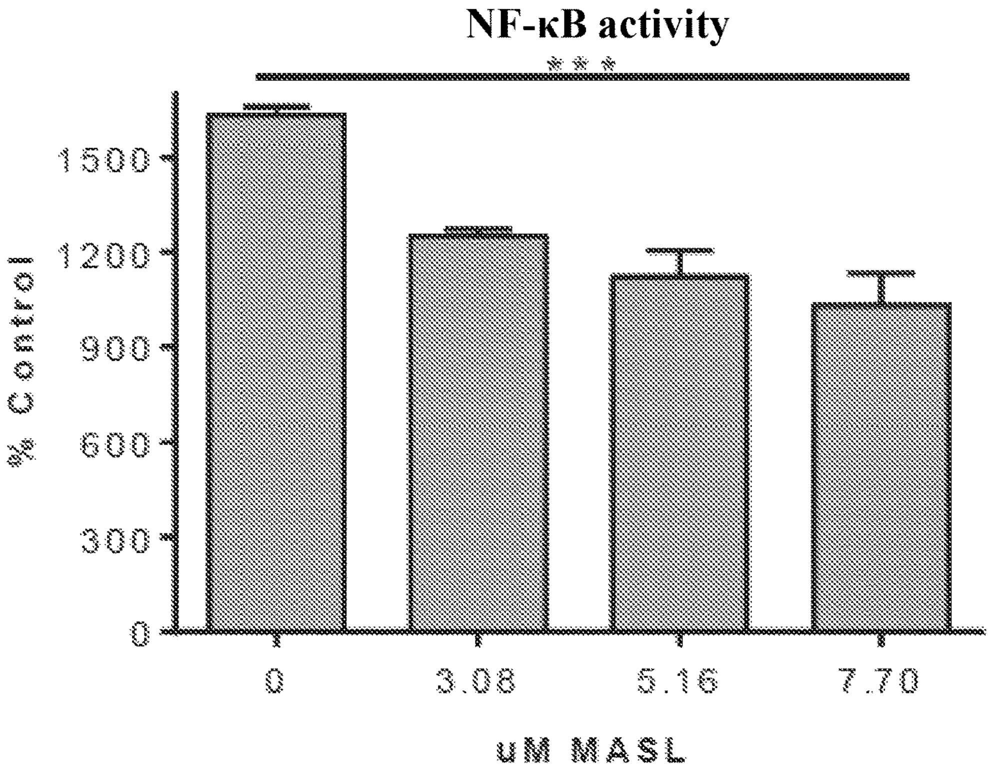
FIG. 6: MASL inhibits NF-kB activity. HeLa cells transfected with a NFkB Luciferase reporter construct were treated with MASL for 5 hours as indicated. Luminescence was normalized to untreated nontransfected control cells and shown as percent control (mean±SEM, n=2). Asterisks indicate p<0.001 by ANOVA.

The pilot data indicate that MASL inhibits NF-kB signaling activity. NF-kB (nuclear factor kappa-light-chain-enhancer of activated B cells) regulates cytokine expression and inflammatory immune response to infection. Accordingly, NF-kB signaling has been implicated in control of ACE2 expression and COVID-19 inflammatory pathologies. NF-kB activity has been found to induce ACE2 expression in response to proteinuria and hyperoxia. The pilot data indicate that MASL significantly inhibits NF-kB activity in human epithelial cells as shown in FIG. 6.

The role of NF-kB in the effects of MASL on ACE2 expression was examined. HSC2 cells were transfected with an inhibitor of nuclear factor kappa-B kinase subunit beta (IKK2) construct with serine to glutamate mutations. This $IKK2_{CA}$ construct promotes activation and nuclear translocation of the NF-kB p65 subunit to drive activation of the canonical NF-kB pathway. This construct can ameliorate the ability of MASL to inhibit ACE2 expression if mediated by NF-kB. These effects were evaluated by reporter assay as shown in FIG. 6, and results were confirmed by qRT-PCR and Western blotting of ACE2 mRNA and protein. These effects in a variety of oral epithelial cells were examine obtained from patients as described herein to evaluate the generality of these effects.

Figure 7A:
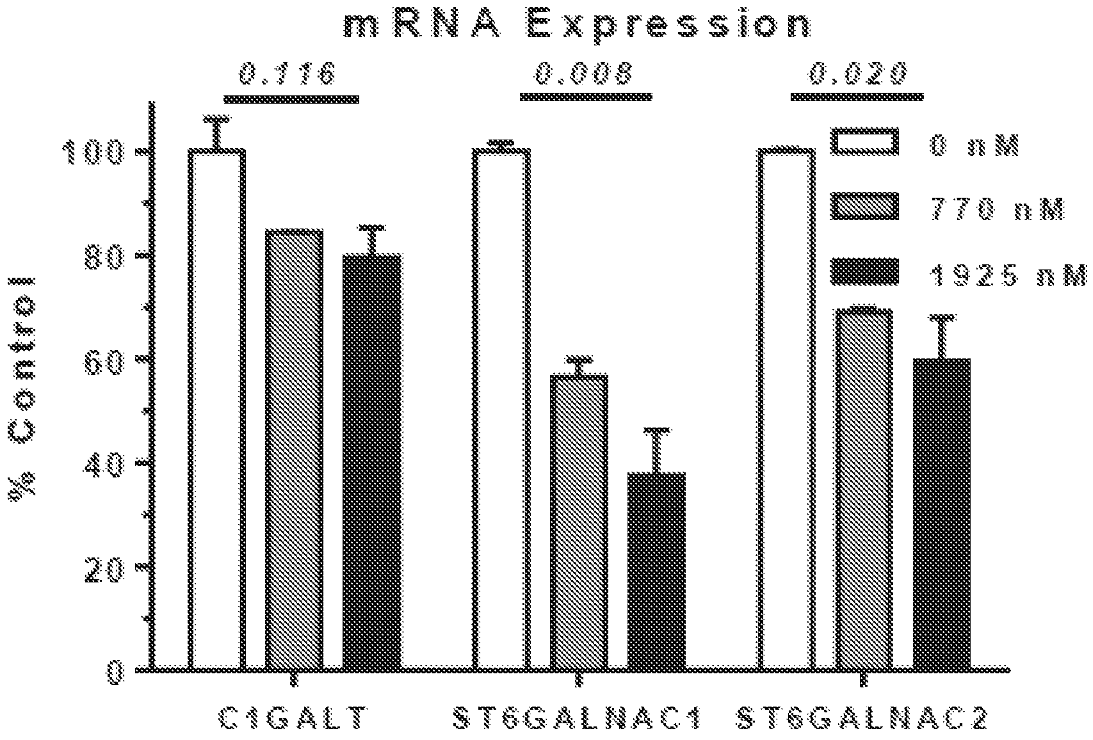
FIGS. 7A-7B: MASL inhibits the expression of glycosylases needed for glycosylation of proteins with sialic acid.
Figure 7B:
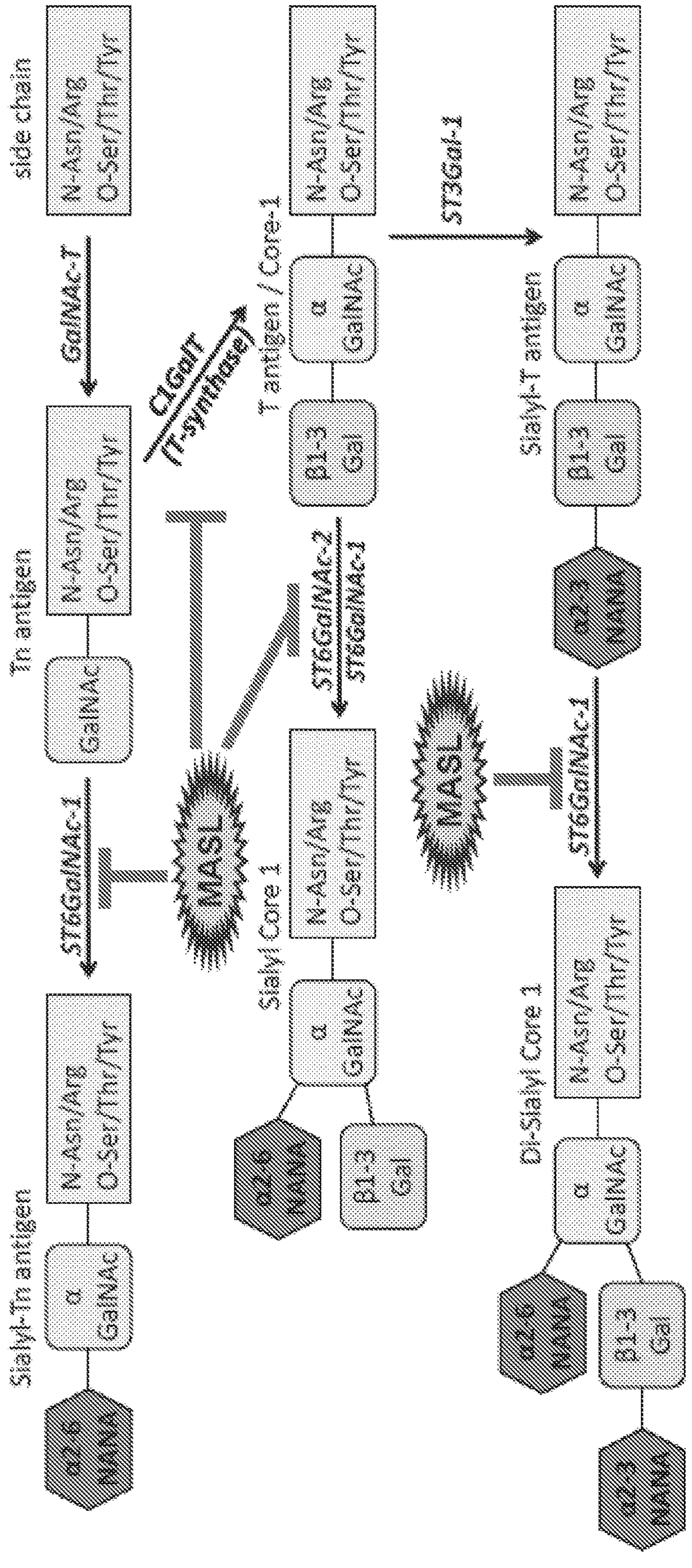

The pilot data indicate that MASL inhibits the expression of glycosylases needed for ACE2 and spike protein sialic acid modification. SARS-CoV-2 spike and host ACE2 proteins are both heavily glycosylated with sialic acids needed for host-viral interactions. The human ACE2 receptor contains at least 10 moieties containing sialic acid (Neu5Ac or NANA) residues, and the SARS-CoV-2 spike protein also contains several sialic acid residues. These modifications are catalyzed by the enzymes GalNAc-T, ST6GalNAc-1, and ST6GalNAc-2. The pilot data indicate that MASL inhibits the expression of these enzymes and thus may inhibit sialic acid modification of ACE2 and spike proteins produced by human oral squamous cells as shown in FIG. 7.

The effects of MASL on ACE2 glycosylation were analyzed. Protein was extracted from cells and digested with trypsin and possibly other endopeptidases to obtain a complete set of peptide fragments which may be enriched for glycopeptides with Mix ZIC glycocapture resin. Peptides were resolved by nanoflow UPLC through an Easy-nLC1000 Nanocolumn and packed with ReproSil-Pur C18-AQ resin and analyzed by Q Exactive MS/MS with an Obitrap Fusion Lumos mass spectrometer. Raw MS files were then analyzed with Protein Metrics Byonic software to identify the location and saccharide composition of glycosylation sites as previously described. This approach was utilized to compare glycosylation of cells treated with different concentrations of MASL to controls. In certain embodiments, MASL can inhibit sialic acid modification of ACE2, and possibly spike protein, in human oral epithelial cells.

Figure 8:
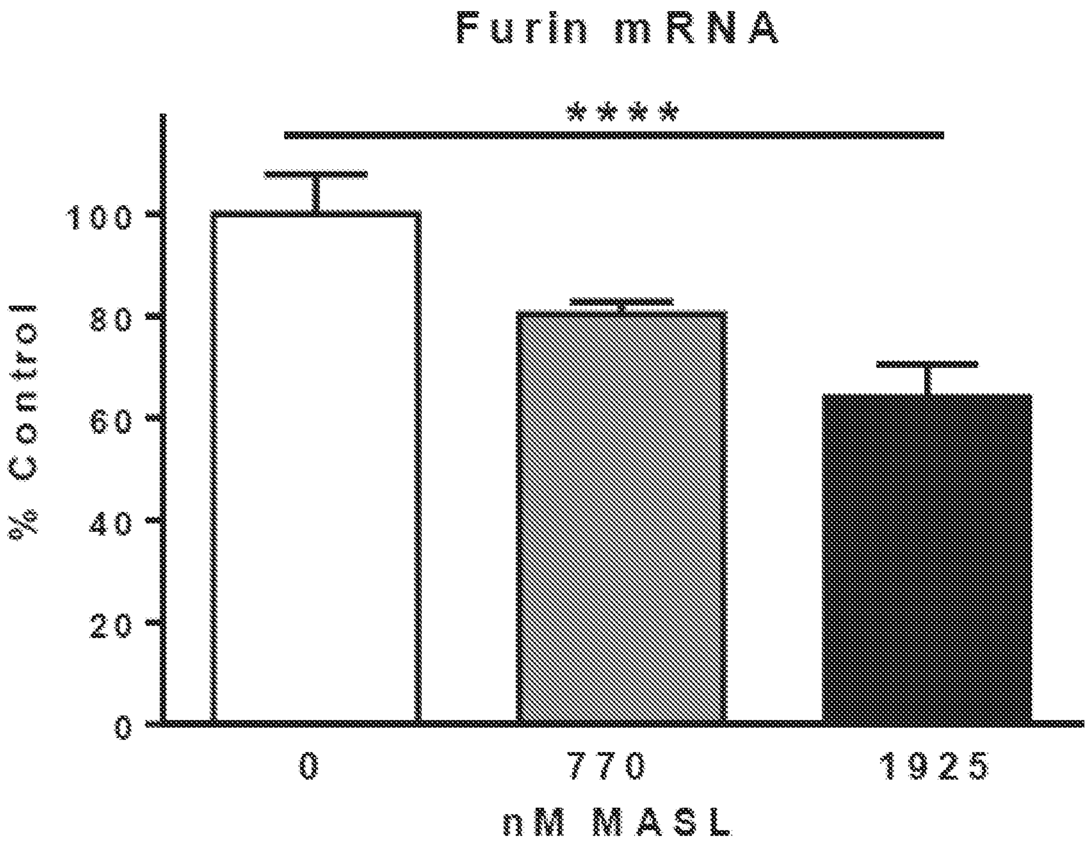
FIG. 8: MASL inhibits furin mRNA expression. HSC2 cells treated with 0, 770, or 1925 nM MASL for 12 hours were examined by RNA Seq. Data are shown as percent of untreated controls (mean±SEM, n=2). Quadruple asterisks indicate p<0.0001 by ANOVA.

The effects of MASL on furin expression were evaluated. The furin protease cleaves the SARS-COV-2 spike protein at the cell membrane to promote membrane fusion and viral endocytosis as shown in FIG. 2. The pilot data indicate that MASL inhibits furin expression in OSC cells as shown in FIG. 8. Western blot analysis were performed on cells and conditioned media to determine how MASL affects intracellular secreted furin levels in HSC2 cells. Additional cells were also employed in this study to evaluate the generality of the findings. MASL can be employed to inhibit SARS-CoV-2 viral entry if it can effectively inhibit furan production at physiologically relevant levels.

In certain embodiments, MASL inhibits NF-kB activity to reduce ACE2 expression in human oral epithelial cells. However, other pathways may be involved. For example, casein kinase 2 (CK2) promotes NF-kB and Wnt signaling to increase ACE2 expression in human type 2 pneumocytes (A549 cells). Reporter constructs were used to investigate the effects of MASL on Wnt, and possibly other pathways such as API if effects on NF-kB are negative or inconclusive. MASL might also inhibit glycosylation and disrupt ACE2 trafficking instead of, or in addition to, decreasing ACE2 expression. IF microscopy was used to visualize ACE2 location and evaluate this effect. HSC2 cells are used in the pilot studies and serve as a representative model system. The pilot data indicate that MASL inhibits PDPN expression in addition to ACE2 (see FIG. 5). Interestingly, MASL also targets PDPN which is expressed on type 1 pneumocytes in the lung epithelial airway.

Figure 9A:
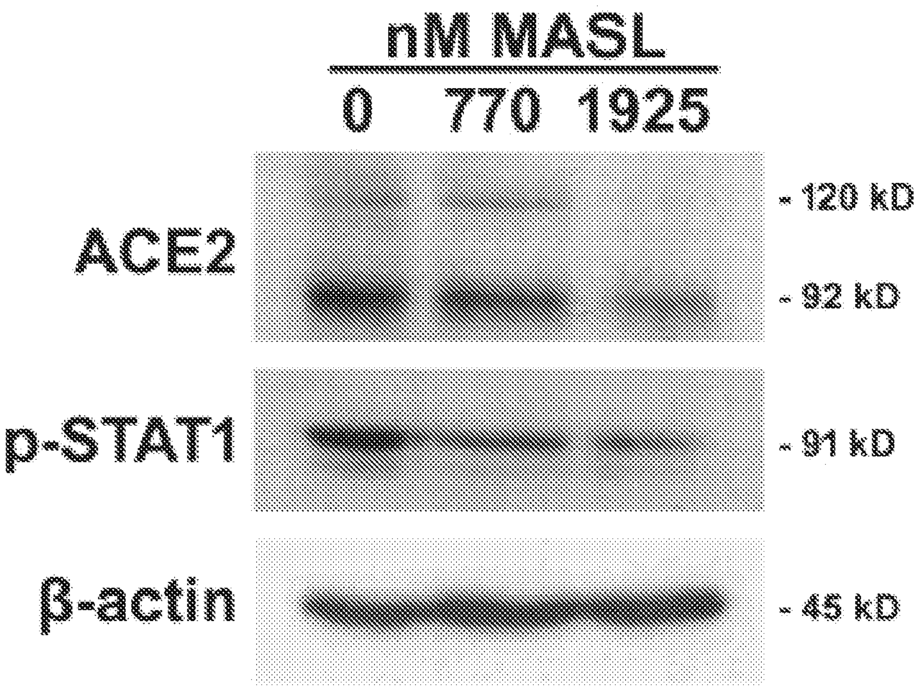
FIGS. 9A-9B: MASL inhibits ACE2 expression and STAT1 activation.
Figure 9B:
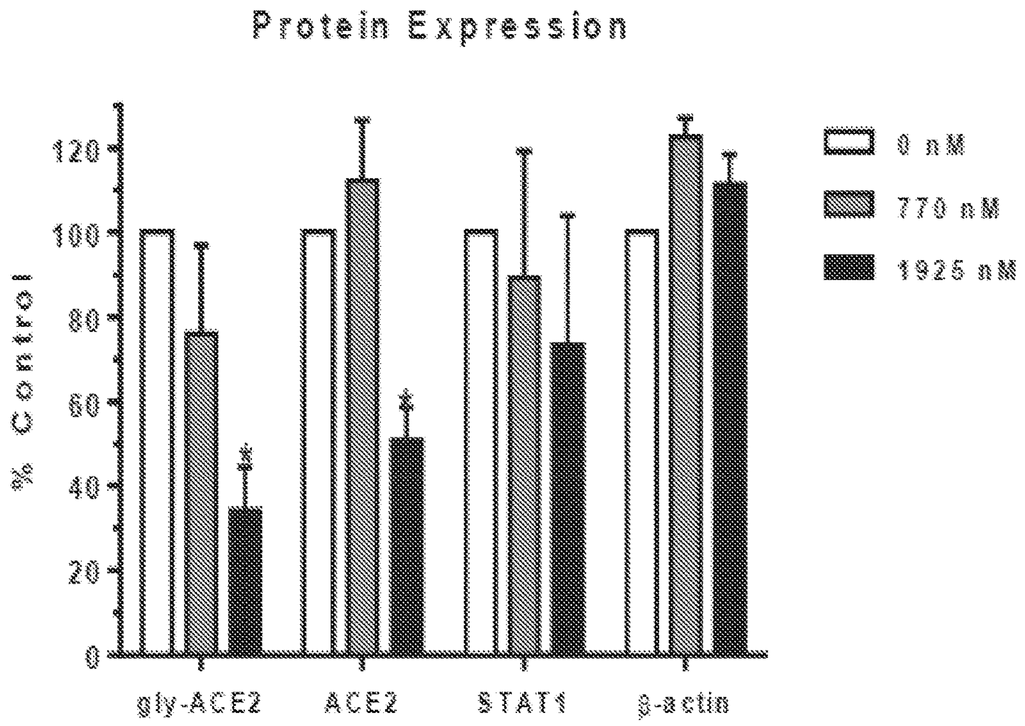
Figure 10A:
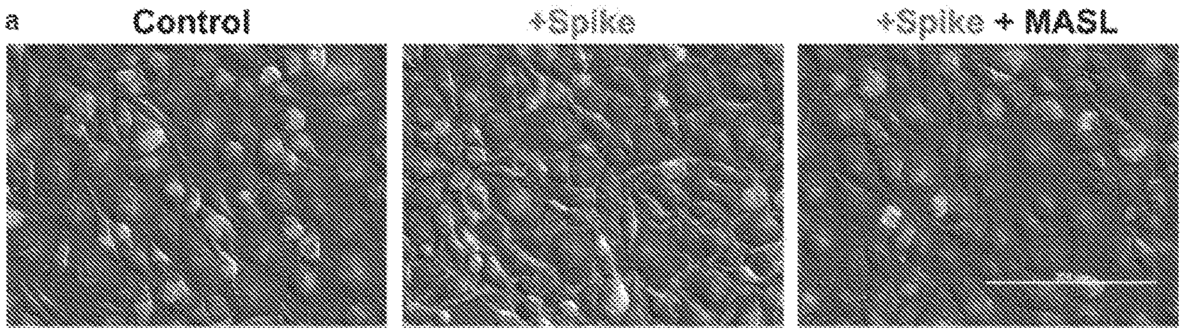
FIGS. 10A-10B: MASL inhibits SARS-CoV-2 spike protein binding to OSCC cells.
Figure 10B:
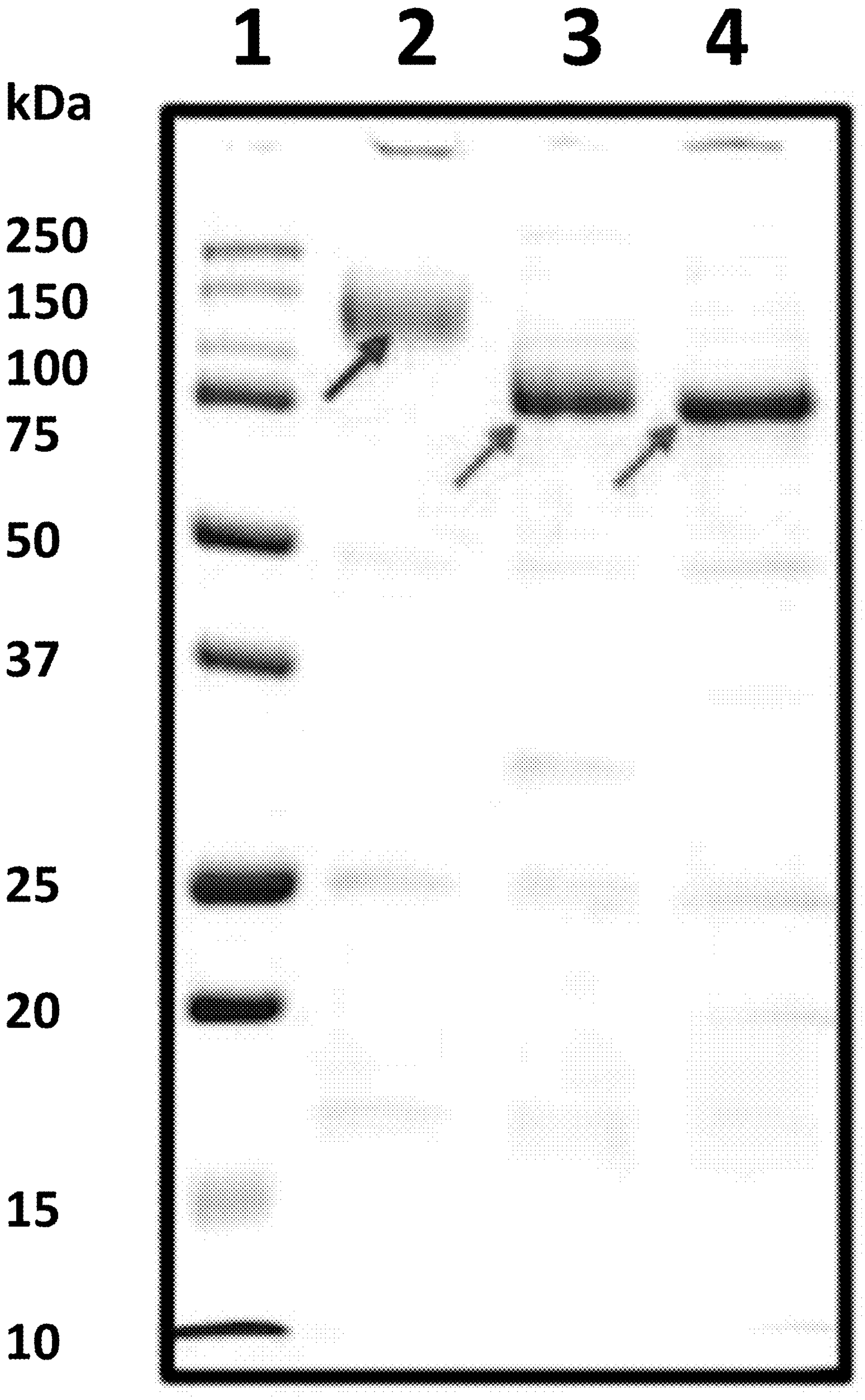

Example 1-2: Examine the Effects of MASL on SARS-CoV-2 Spike Protein Binding to ACE2 Receptors and Infection of Oral Squamous Cells The supporting data indicate that: (1) SARS-CoV-2 spike protein and ACE2 are glycosylated with sialic acid moieties; (2) MASL targets sialic acid modified receptors on OSCs; and (3) MASL inhibits SARS-CoV-2 spike protein binding to OSCs. Lectins can be taken orally to treat, ameliorate, and/or prevent diseases including cancer and viral infections. MASL targets sialic acid modified receptors to inhibit cancer progression and/or inflammation. Therefore, MASL should target the human ACE2 receptor and SARS-CoV-2 spike protein which both contain several extracellular sialic acid residues. *Maackia amurensis* lectin binds to α-2,3 and α-2,6 O-linked sialic acid residues on host receptor glycoproteins to inhibit sapovirus infection. Interestingly, sapovirus utilizes a plus-sense stranded single RNA genome like SARS-CoV-2. Consistent with the mRNA data shown in FIG. 5 and FIG. 7, the pilot data indicate that 12 hours treatment with less than 2 μM MASL inhibits ACE2 protein expression and glycosylation by over 50% as shown in FIG. 9. In addition, the pilot studies also indicate that MASL effectively inhibits the ability of the viral spike protein to target human oral epithelial cells as shown in FIG. 10. While Example 1-1 investigates how MASL inhibits ACE2 production and glycosylation, Example 1-2 investigates how MASL affects ACE2-spike protein interactions to inhibit SARS-CoV-2 infection.

In the designed clinical trials, the effects of MASL on SARS-CoV-2 infection in cell culture are investigated. Up to 50 OSC cell lines obtained from patients enrolled in a clinical trial independent of this application were utilized. Spike protein and intact virus werelabeled red with Alexa555, MASL far red with Alexa647, and ACE2 antibody green with Alexa488. These reagents were incubated with OSC cells for 1 hour, wash, and visualize spike protein virus, receptor, and MASL by live and fixed cell imaging. These fluorescent signals ewre quantitated to examine how MASL affects the binding of spike protein and virus entry in OSC cells. Viral RNA production were also examined by qRT-PCR in conditioned media and cells treated in these experiments. These data were used to determine MASL concentrations needed to inhibit SARS-CoV-2 infection. In certain embodiments, MASL inhibits viral targeting and/or replication in this cell culture model.

Direct interactions between purified spike protein and MASL are characterized. Forster resonance energy transfer between Alexa674-labeled MASL and Alexa555-labeled spike protein is measured in a spectrofluorometer. Label-free spike-MASL binding are also measured using surface plasmon resonance. The His-tagged spike protein is immobilized on a Biacore sensor chip, and varying concentrations of MASL are injected over the surface to derive the equilibrium dissociation constant (Kd).

How MASL affects the ability of SARS-CoV-2 virus to infect OSCs alone and in combination with other anti-COVID agents were determined. Physiologically relevant MASL concentrations not toxic to normal cells alone and in combination with viral protease blockers lopinavir/ritonavir, and RdRP blockers remdesivir and favipiravir were examined. In certain embodiments, these agents produce additive, and in certain embodiments synergistic effects, with MASL to inhibit SARS-CoV-2 production in OSC cells. These agents were used to suppress viral proliferation (FIG. 2, Panel E) and treat COVID-19 patients.

Example 1-3: MASL on SARS-CoV-2 Induced OSC Inflammation

COVID-19 kills about 2% of infected individuals. This morality rate is over 10 times higher than that of the seasonal influenza virus. Severe acute respiratory distress syndrome (ARDS) is a major COVID-19 morbidity.

COVID-19 instigates chronic inflammation resulting in a "cytokine storm" that causes most ARDS mediate deaths. COVID-19 also causes multisystem inflammatory syndrome (MIS) in children and adolescents. This hyper-inflammation leads to multiple organ failure and shock. Treatments for these inflammatory syndromes include parenteral immunoglobulin and steroids with limited efficacy. A clear understanding of COVID induced inflammation illuminates new avenues for treatments that are clearly needed for COVID-19 patients.

Figure 11:
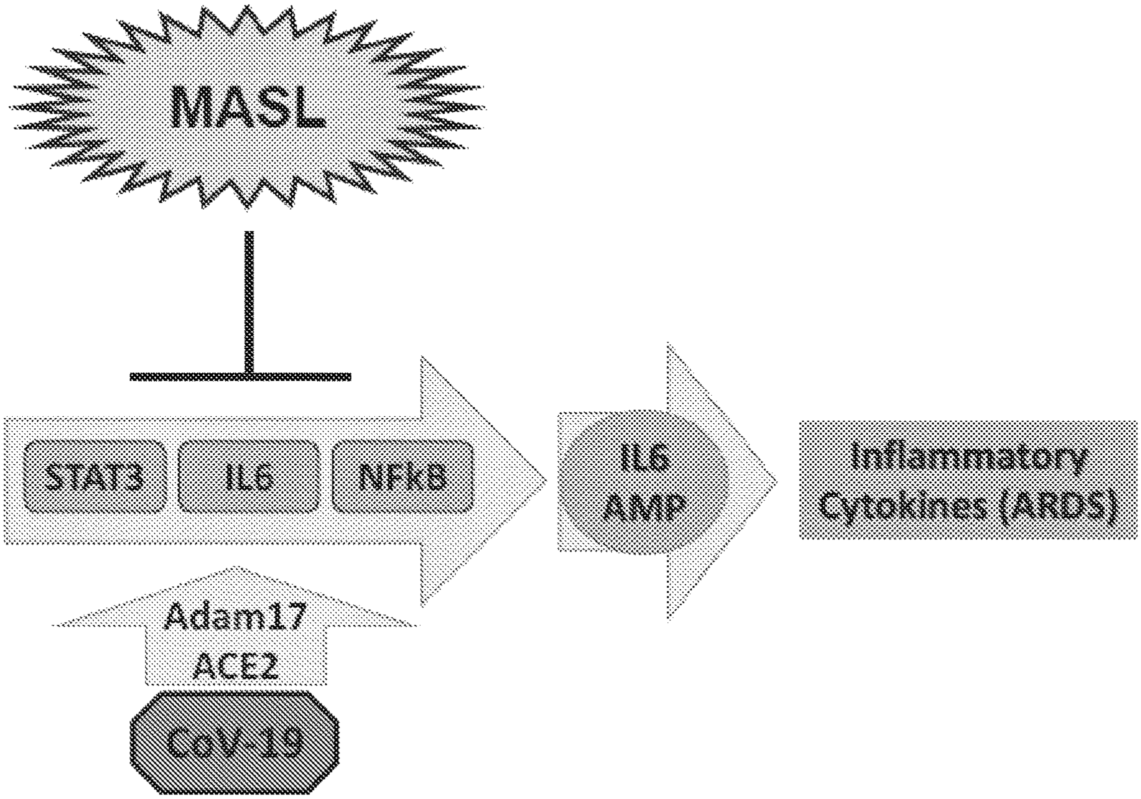
FIG. 11: MASL inhibits COVID-19 induced inflammation. SARS-CoV-2 targets ACE2 and activates ADAM17 which potentiates IL6 to induce STAT3 and NFkB signaling. These factors cooperate to potentiate the IL6 amplifier (IL6-AMP) which induces inflammatory cytokine expression resulting in ARDS.

COVID-19 inflammation shares inflammatory mechanisms with arthritis. Viral infections can cause severe arthritis. Indeed, COVID-19 infection causes arthralgia and myalgia in 15% and 44% of patients, respectively. Molecular pathways leading to COVID-19 and rheumatoid arthritis pathologies are driven by STAT3, IL6, and TNF activation as shown in FIG. 11.

SARS-CoV-2 spike proteins bind to ACE2 receptors on oral mouth and tongue epithelium to enable viral endocytosis, COVID-19 infection, and subsequent inflammation. These infections induce FOXO1 expression in epithelial cells including oral mucosa, which induces the expression of toll-like receptors (TLRs). TLR signaling induces interleukin-36 (IL36) production, which induces IL6 expression. IL6 then goes on to produce inflammatory cytokines in response to infections including tuberculosis in lung epithelial cells. In addition to viral lung inflammation, IL6 signaling also triggers contact dermatitis and psoriasis in keratinocytes, as well as arthritic inflammation in chondrocytes.

Arthritis and COVID-19 inflammation relies on NFkB activation. SARS-CoV-2 binds to ACE2 on lung and oral epithelial cells. ACE2 activates a disintegrin and metalloproteinase 17 (ADAM17) which generates mature inflammatory ligands including IL6. IL6 then activates STAT3 in epithelial cells. STAT3 signaling induces the expression of cytokines including more IL6 and KFkB.

The main inflammatory action triggered by IL6 through STAT3 is to activate NFkB and the IL6 AMP. IL6, STAT3, and NFkB cooperate to induce the IL6 amplifier (IL6-Amp) which hyper-activates NFkB to produce cytokines that cause multiple inflammatory responses as shown in FIG. 11. This occurs in a variety of cells including chondrocytes, intestinal, lung, and dermal epithelium. NFkB can also induce IL6 production to induce vascular inflammation.

Figure 12:
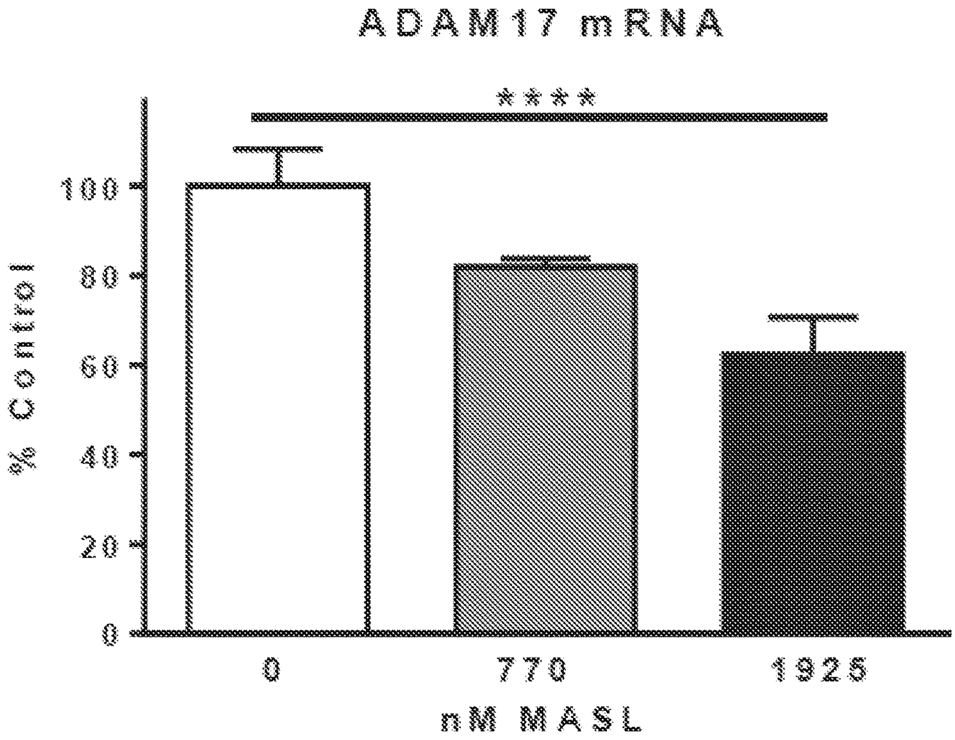
FIG. 12: MASL inhibits ADAM17 mRNA expression. HSC2 cells treated with 0, 770, or 1925 nM MASL for 12 hours were examined by RNA-Seq. Data are shown as percent of untreated controls (mean±SEM, n=2). Quadruple asterisks indicate p<0.0001 by ANOVA.
Figure 13:
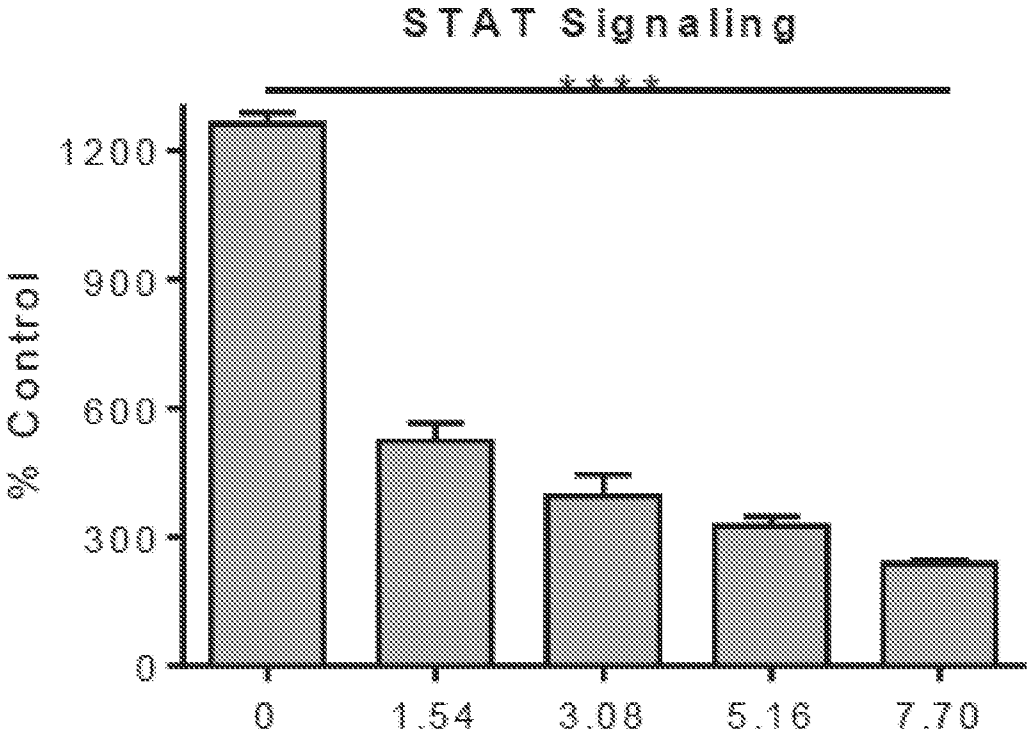
FIG. 13: MASL inhibits STAT activity. HeLa cells transfected with a STAT3 luciferase reporter construct were treated with indicate MASL μM concentrations for 5 hours as indicated. Luminescence was normalized to untreated nontransfected control cells and are shown as percent control (mean±SEM, n=2). Quadruple asterisks indicate p<0.0001 by ANOVA.

The pilot data indicate that MASL inhibits IL6-Amp activation. As described herein, ACE2 potentiates ADAM17 to activate cytokines that promote inflammation. The pilot data indicate that MASL inhibits ADAM17 expression as shown in FIG. 12. In addition, the pilot data indicate that MASL also inhibits the JAK-STAT pathway that is critical for IL6-activation and inflammatory signaling as shown in FIG. 13. Moreover, the pilot data indicate that MASL inhibits NFkB signaling as shown in FIG. 6. Taken together, these data indicate that MASL inhibits ADAM17 expression and three major components of the IL6 amplifier—STAT3, IL6, and NFkB—as illustrated in FIG. 11. Moreover, MASL attenuates inflammatory NFkB signaling and inflammation in chondrocyte cell structure, and can be administered orally to alleviate arthritis progression in mice.

Figure 14A:
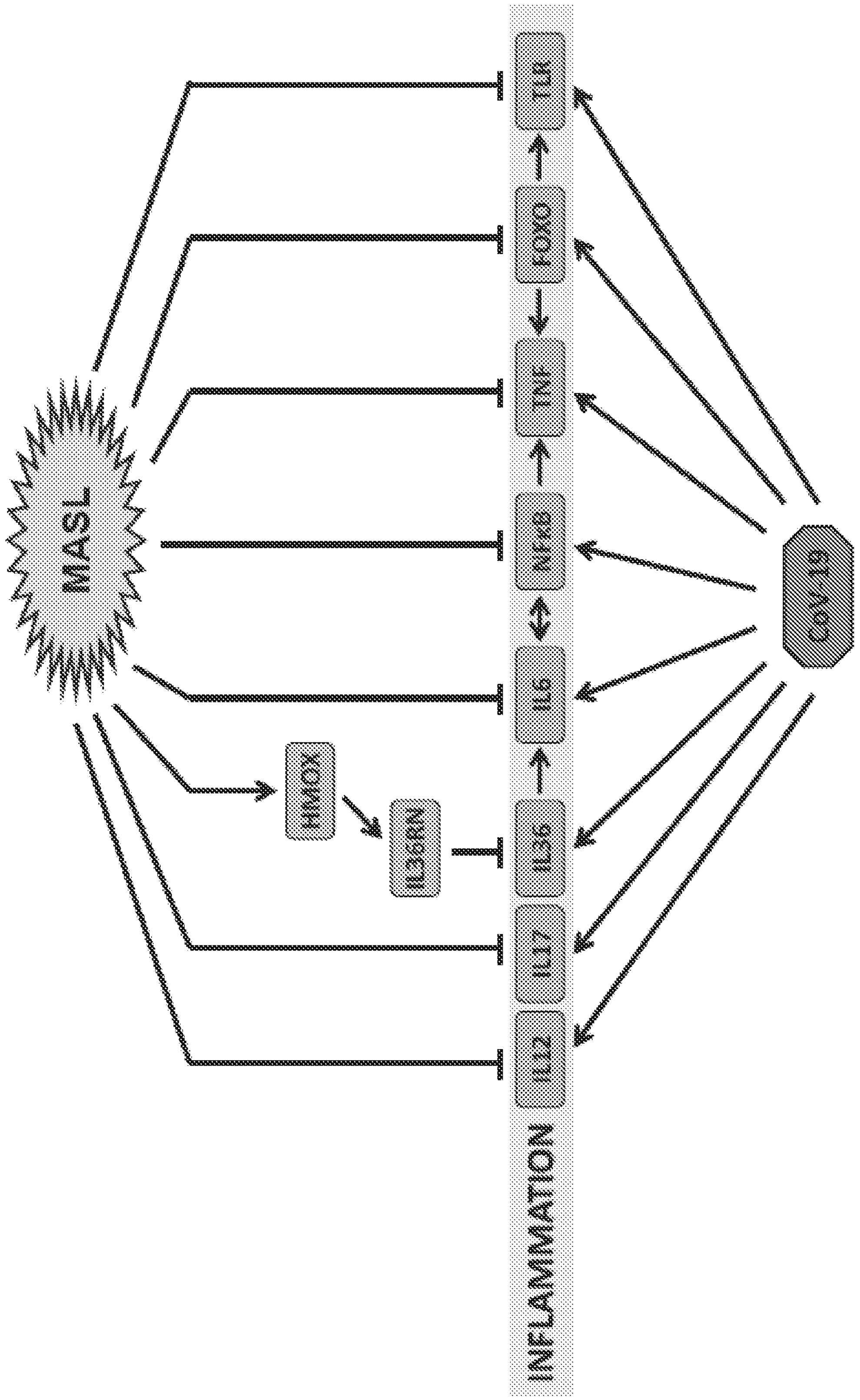
FIGS. 14A-14B: Effects of COVID-19 and MASL on inflammation.
Figure 14B:
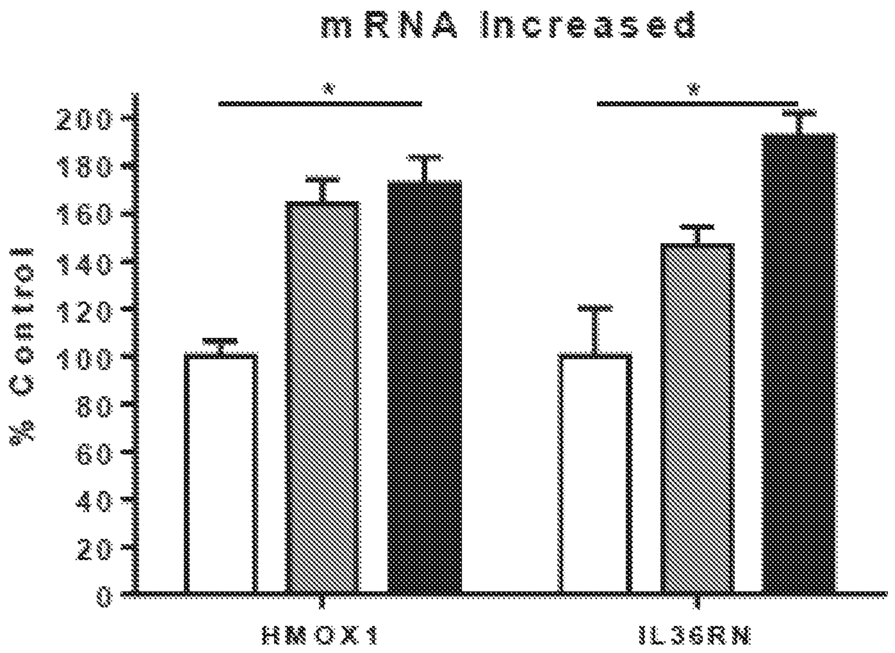
Figure 14B:
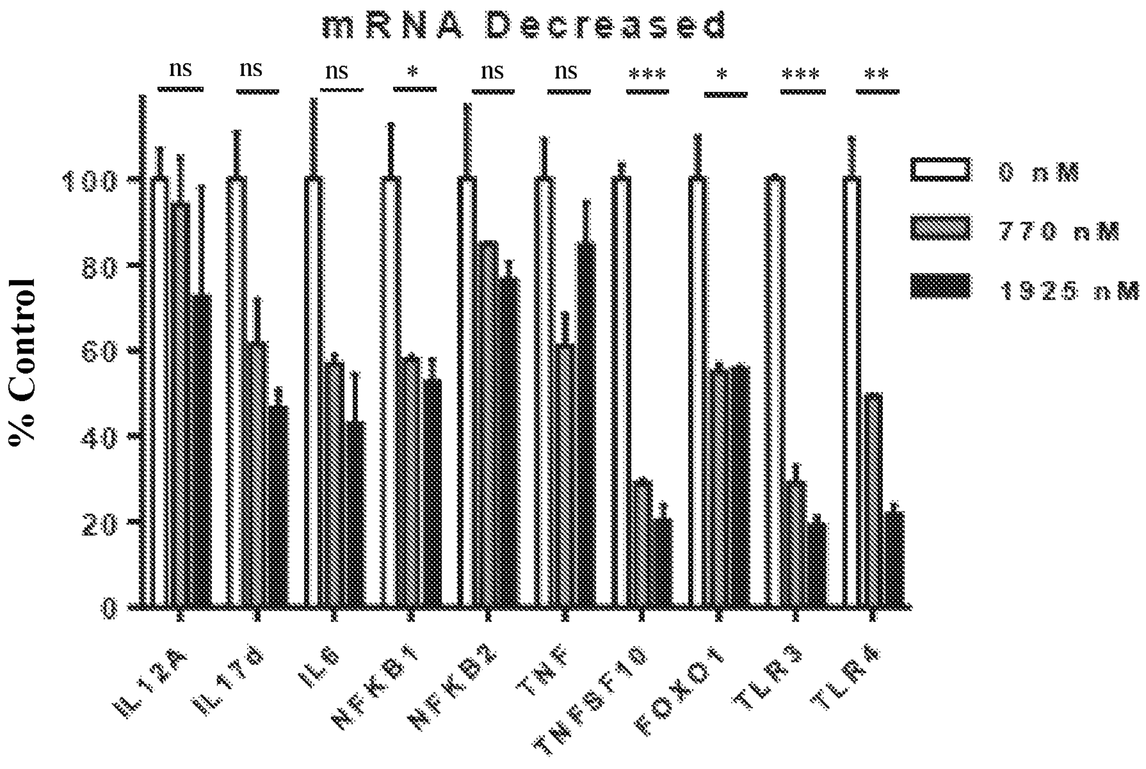

The pilot data indicate that MASL inhibits inflammatory cytokines. In addition to inhibiting IL6, NFkB and STAT signaling, and possibly as a result of IL6-Amp suppression, MASL also decreases expression of cytokines including IL12, IL17, IL36, TNF, LTRs, and FOXO1 as shown in FIGS. 14A-14B. IL12 and IL17 are potent inflammatory cytokines involved in COVID, arthritis, and psoriasis progression. Therefore, inhibition of these cytokines can control overall inflammatory response. Interestingly, MASL has been found to suppress interleukin induced psoriatic inflammation in reconstituted epidermis.

The pilot data indicate that MASL increases heme oxygenase 1 (HMOX1) and interleukin 36 receptor antagonist (IL36RN) expression in OSCs. Infections trigger FOXO1 expression in epithelial cells including oral mucosa, which induces TLRs to increase IL36 in order to promote IL6 expression. HMOX expression induces IL36 RN production to inhibit interleukin and NFkB activity, which would otherwise lead to cytokine production and inflammation. MASL appears to utilize HMOX to induce IL36RN expression in order to inhibit IL6 mediated inflammation as shown in FIGS. 14A-14B. These data are relevant to COVID-19. The IL6 antibody blocker tocilizumab was found an effective treatment for CAR-T cell induced cytokine storm, and has been adopted as a treatment for COVID-19 inflammation.

The present study elucidates the effects of MASL on SARS-CoV-2 induced inflammation. The effects of MASL on inflammatory signaling pathways in cultured OSCs, as well as the oral cavity and vascular circulation of COVID-19 patients were analyzed. MASL inhibits the production of inflammatory cytokines by OSCs, and can be administered orally to reduce inflammation of oral mucosa and systemic systems in COVID-19 patients.

In certain embodiments, MASL inhibits inflammatory cytokine production and signaling in response to SARS-CoV-2 infection in this cell culture model.

Example 2: Comprehensive Study

SARS-CoV-2 has infected over 125 million people and caused over 2.7 million deaths around the world in just 16 months (as of March 2021). The SARS-CoV-2 spike protein targets the angiotensin converting enzyme 2 (ACE2) receptor on host cells. This interaction is mediated by a receptor binding domain (RBD) in the S1 portion of the spike protein that recognizes the human ACE2 extracellular domain. Transmembrane protease serine 2 (TMPRSS2) and furin cleave a polybasic sequence to unlink the S1 and S2 domains in the SARS spike protein to promote virial cell entry.

Lung epithelium, primarily T2 but also Ti cells, are considered prime SARS-CoV-2 infection sites. However other cells can be infected, including salivary gland and nasal epithelial cells. ACE2 and furin protease are also highly expressed by human oral squamous epithelial cells of the mucosa and tongue where they can act as viral infection sites. SARS-CoV-2 activates inflammatory pathways involving STAT3, IL6, and TNF that cause inflammation leading to pathologies including acute respiratory distress syndrome (ARDS).

The SARS-CoV-2 spike and host ACE2 proteins are both heavily glycosylated with sialic acids needed for viral infection. The SARS-CoV-2 spike protein has at least 22 N-linked glycosylation sequons per protomer, and about 15% of these glycans contain at least one sialic acid residue. The human ACE receptor contains 7N-linked and 3 O-linked glycans, and they all contain sialic acid residues.

Lectins recognize specific glycosylation motifs, and can be used as antiviral agents. In particular *Maackia amurensis* seed lectin (MASL) has a strong affinity for sialic acid modified proteins, and targets specific receptors to inhibit viral infection, cancer progression, and inflammation. Indeed, the effect of MASL on oral squamous cell carcinoma is being investigated in Phase I human clinical trial. However, effects of MASL on SARS-CoV-2 infection and inflammatory pathways have not been described. Here, the present study demonstrates that MASL targets the ACE2 receptor, inhibits SARS-CoV-2 spike binding, and decreases the expression of ACE2, furin, sialic acid glycosylases, and inflammatory cytokines in human OSCC cells. In addition, MASL also inhibits SARS-CoV-2 infection of mammalian kidney epithelial cells. These data suggest that MASL offers an opportunity to target oral epithelial cells by oral administration to help combat SARS-CoV-2 infection and disease progression.

Example 2-1: Results of the Comprehensive Study

SARS-CoV-2 spike proteins binds to ACE2 receptors on oral mouth and tongue epithelium to enable viral endocytosis, COVID-19 infection, and subsequent inflammation. HSC-2 OSCC cells were used as a model system for this study. These cells were derived from the mouth floor of a 69 year old male and are HPV negative. *Maackia amurensis* seed lectin (MASL) targets sialic acid modified receptors on these cells within 2 min of exposure.

Figure 15A:
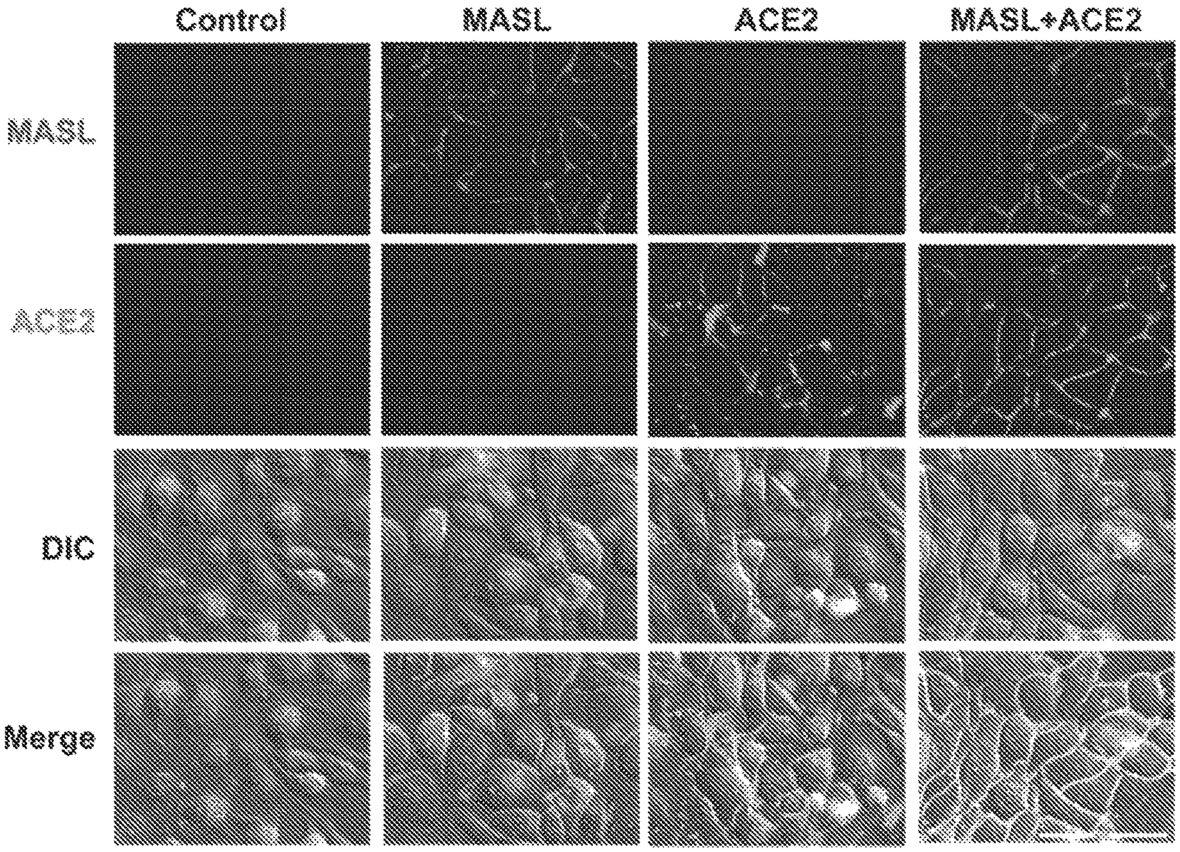
FIGS. 15A-15E demonstrate that MASL colocalizes with ACE2 and inhibits SARS-CoV-2 spike protein binding to OSCC cells, in accordance with some embodiments.
Figure 15B:
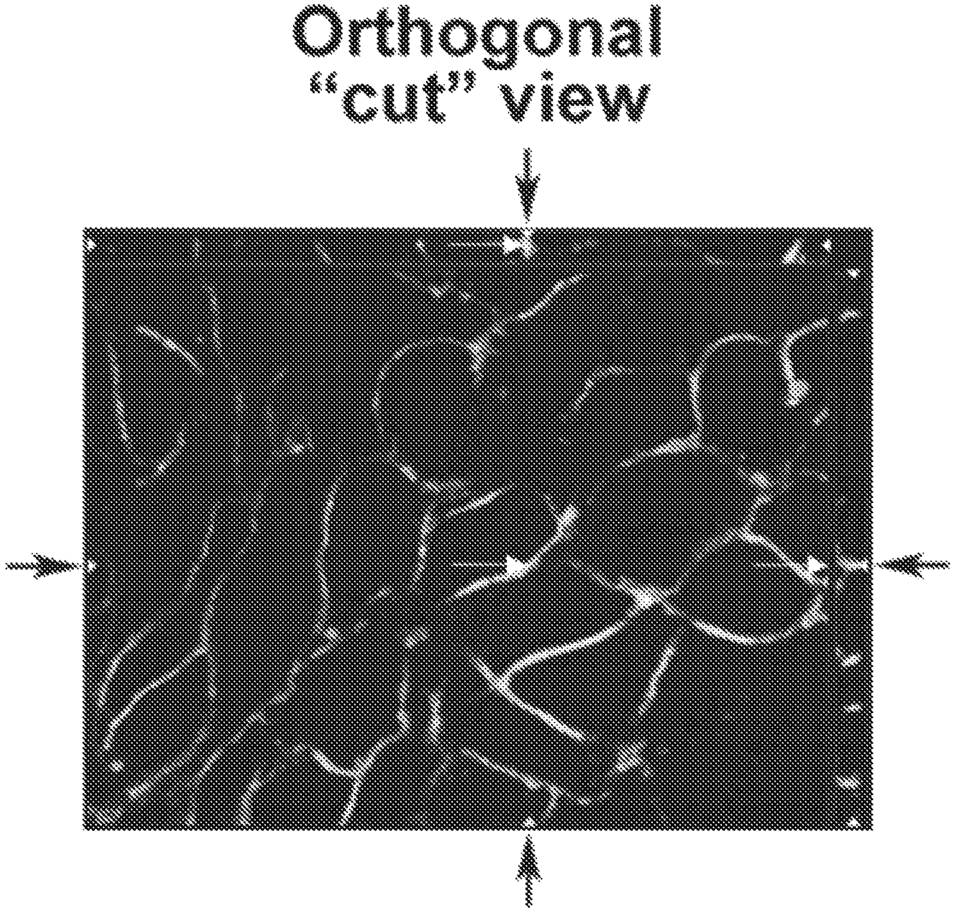
Figure 15C:
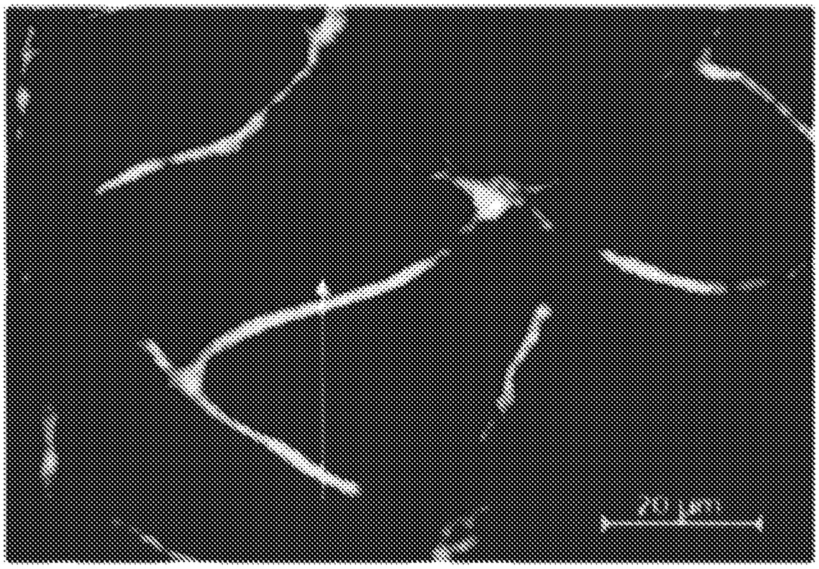
Figure 15C:
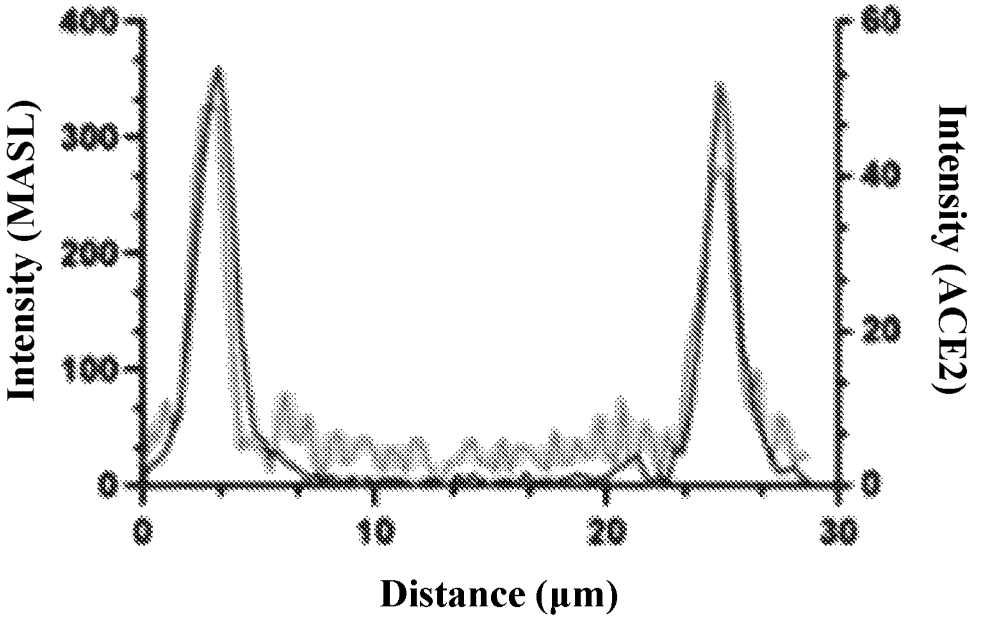
Figure 15D:
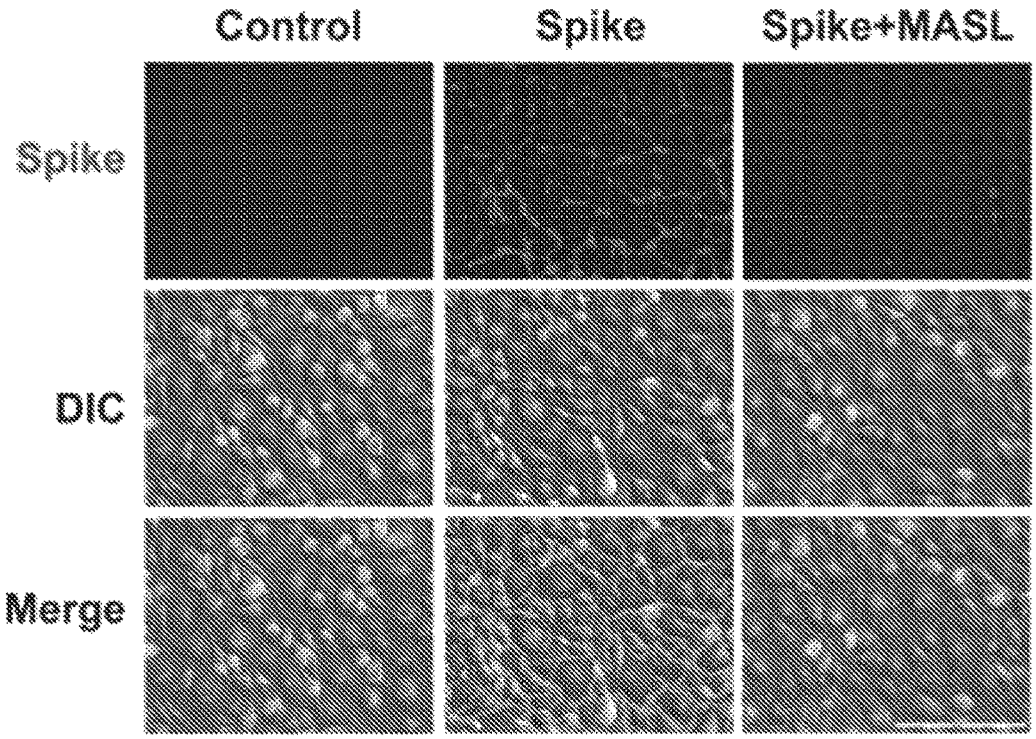
Figure 15E:
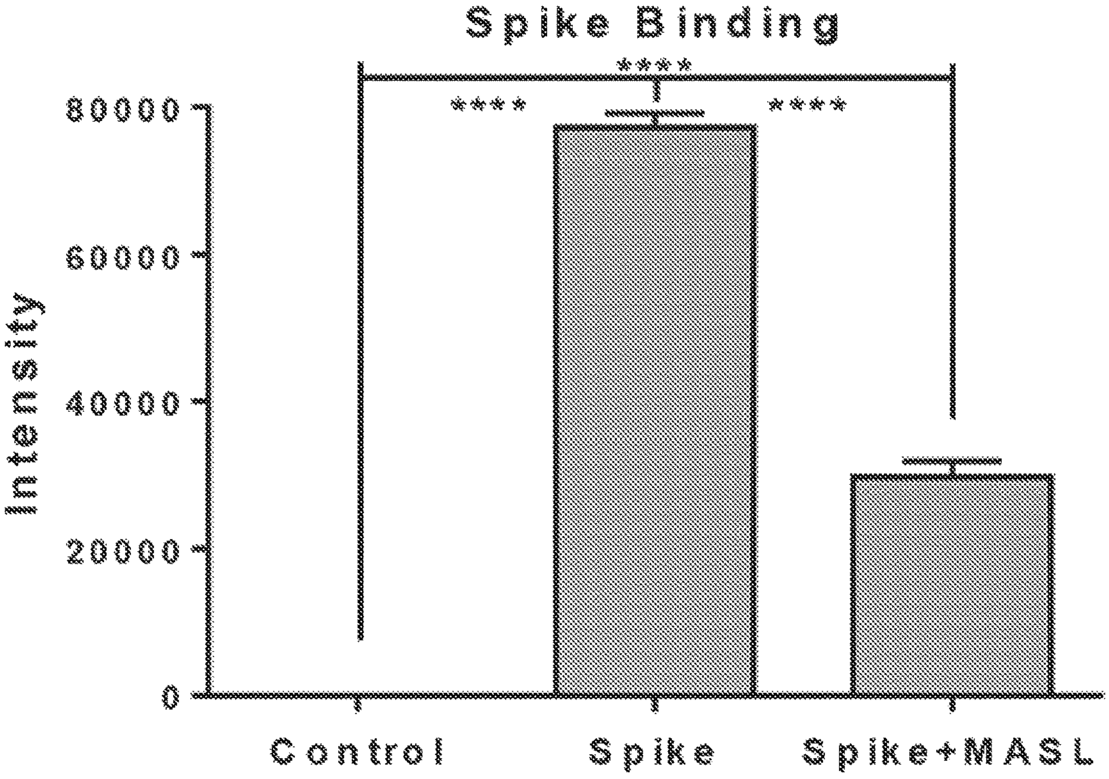

*Maackia amurensis* lectin binds to α-2,3 and α-2,6 O-linked sialic acid residues on host cell receptor glycoproteins to inhibit sapovirus infection. The SARS-CoV-2 spike protein and human ACE2 receptor are both decorated with sialic acid residues needed for viral infection. In certain embodiments, MASL can associate with the human ACE2 receptor and/or the SARS-CoV-2 spike protein to prevent and/or minimize infection. Results from live cell imaging experiments indicate that MASL colocalizes with the ACE2 receptor on HCS-2 cells as shown in FIGS. **15A*a*-15C. Accordingly, MASL effectively inhibited the ability of viral spike protein to target HSC-2 cells as shown in FIGS. 15D-15E**.

Figure 16A:
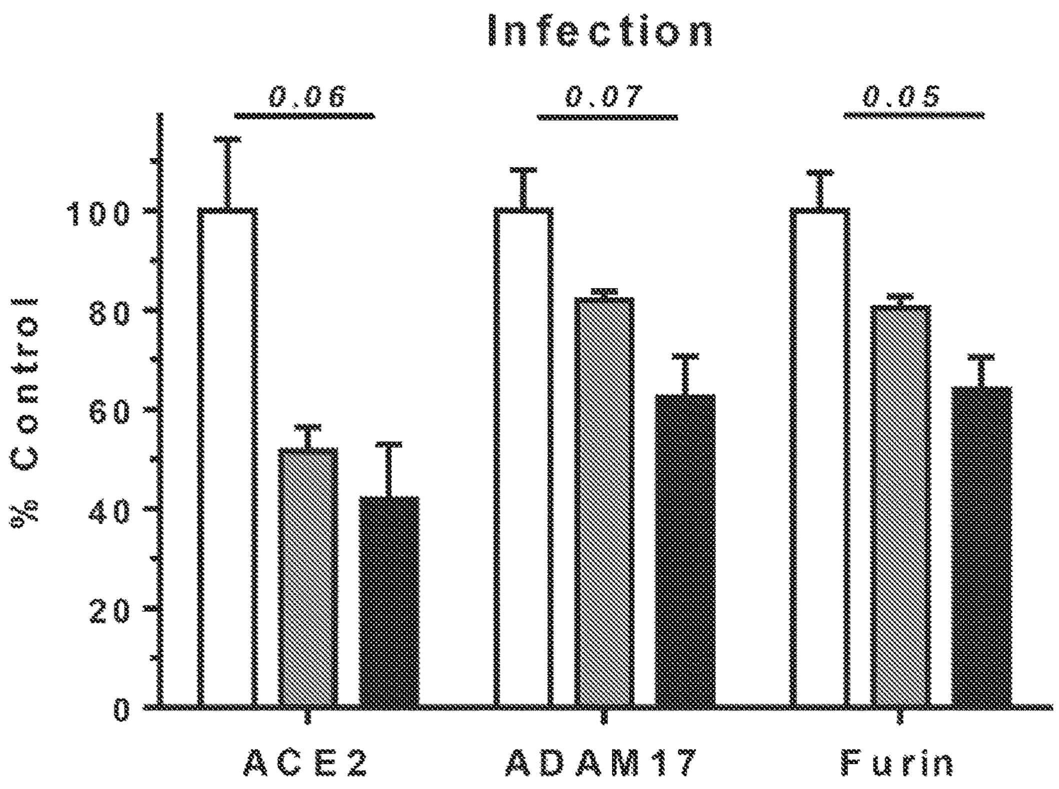
FIGS. 16A-16C demonstrate that MASL affects expression of genes involved in SARS-CoV-2 infection and inflammation, in accordance with some embodiments.
Figure 16B:
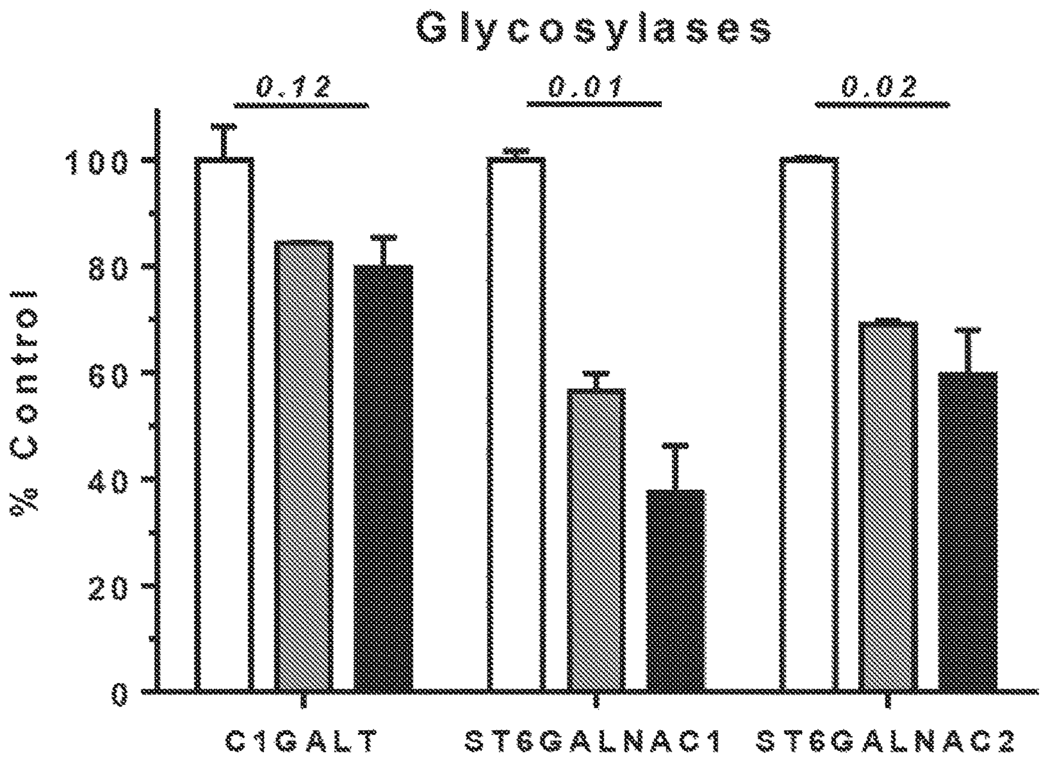
Figure 17A:
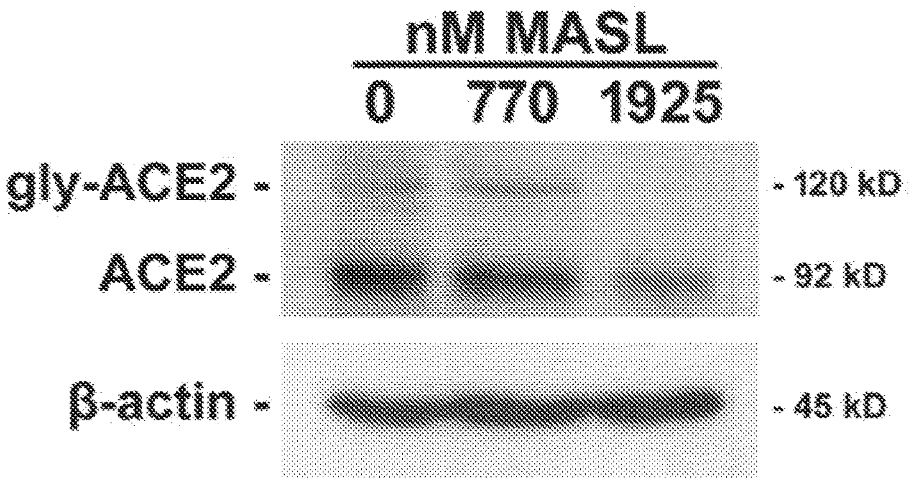
FIGS. 17A-17B demonstrate that MASL inhibits ACE2 receptor expression and glycosylation, in accordance with some embodiments.
Figure 17B:
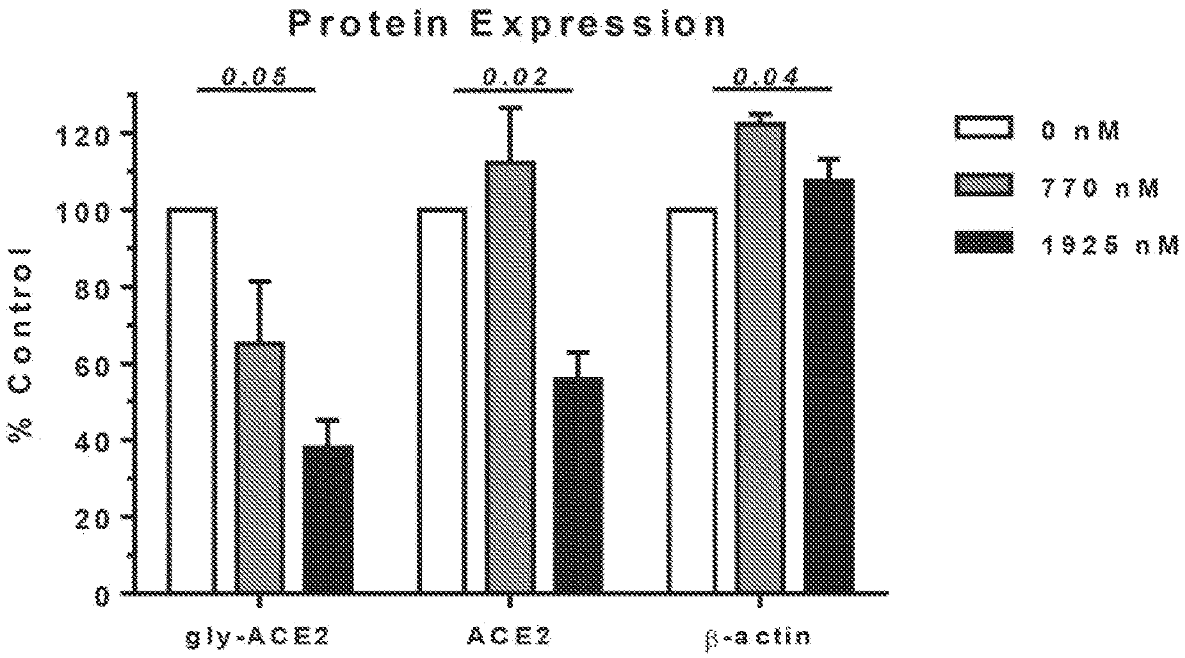

In addition to interfering with interactions between spike and ACE2 proteins, MASL appears to inhibit ACE2 expression and glycosylation. MASL decreases ACE2 mRNA levels in HSC-2 cells by nearly 50% and 60% at 770 nM and 1925 nM, respectively, as shown in FIG. 16A. The human ACE2 receptor contains at least 10 moieties containing sialic acid (Neu5Ac or NANA) residues. These modifications are catalyzed by the enzymes GalNAc-T, ST6GalNAc-1, and ST6GalNAc-2. As shown in FIG. 16B, MASL inhibits the expression of mRNA encoding these enzymes in a dose responsive manner. Taken together, these results suggest that MASL inhibits ACE2 expression and posttranslational sialic acid modification. These results are confirmed at the protein level by Western blotting. Treatment of cells with 1925 nM MASL for 12 h inhibited ACE2 protein expression and glycosylation by over 50% as shown in FIGS. 17A-17B. In contrast, (β-actin expression, which was used as a control, was either not affected or slightly increased (see FIGS. 17A-17B).

After viral recognition, furin protease cleaves the SARS-CoV-2 spike protein at the cell membrane to promote membrane fusion and viral endocytosis. After furin cleavage, a disintegrin and metalloproteinase 17 (ADAM17) generates mature inflammatory ligands including IL6 in response to SARS-CoV-2 infection. Interestingly, MASL decreased furin and ADAM17 mRNA levels in HSC-2 cells by nearly 20% and 40% at 770 nM and 1925 nM, respectively, as shown in FIG. 16A.

Once activated in response to infection, IL6 activates STAT3 in epithelial cells. STAT3 signaling induces the expression of cytokines including more IL6 and NFκB. IL6, STAT3, and NFκB cooperate to induce the IL6 amplifier (IL6-Amp) which hyper-activates NFκB to produce cytokines that cause multiple inflammatory responses. This occurs in a variety of cells including chondrocytes, intestinal, lung, and dermal epithelium. NFκB can also induce IL6 production to induce vascular inflammation.

Figure 18A:
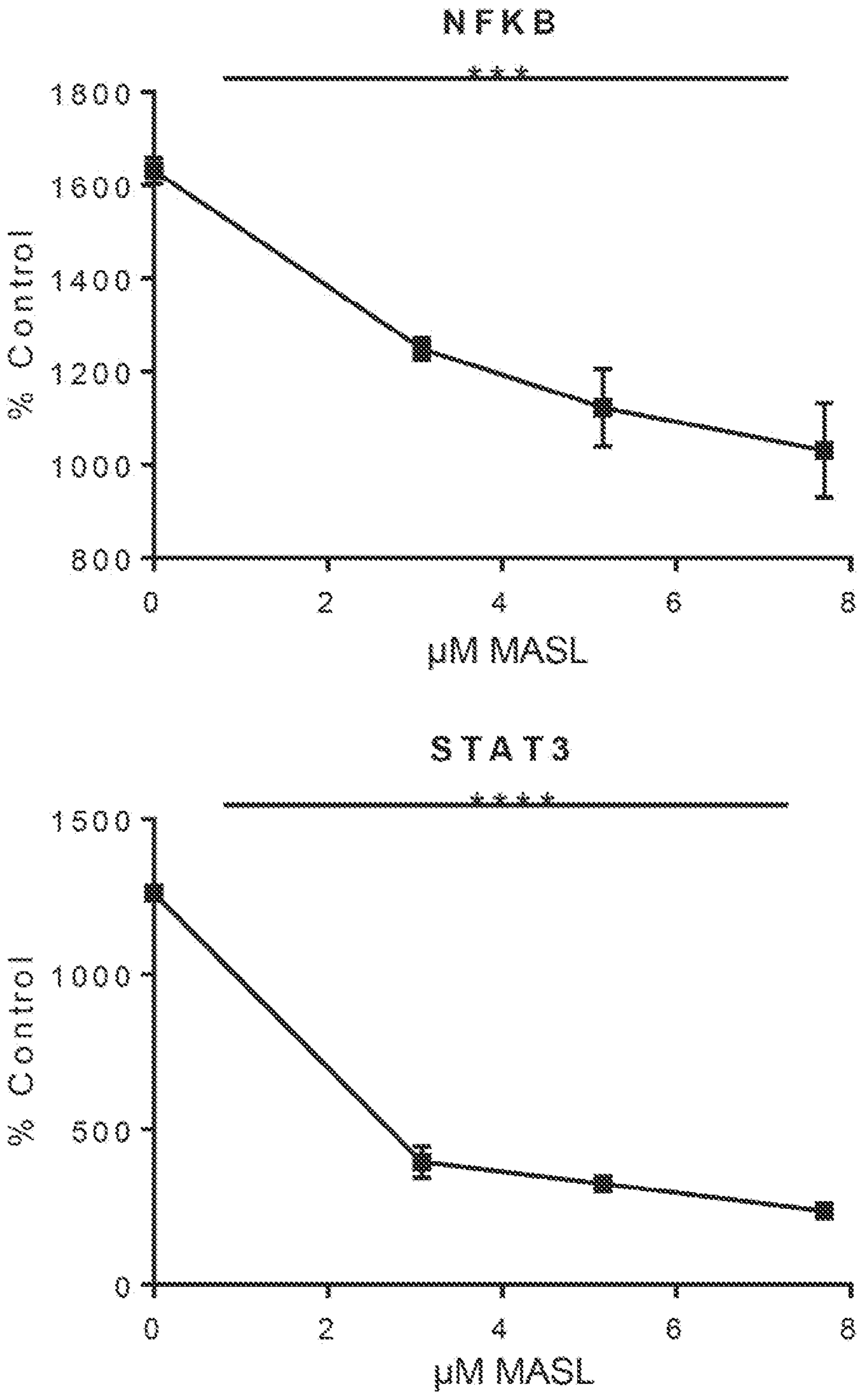
FIGS. 18A-18C demonstrate that MASL affects NFκB and STAT3 transcriptional activation pathways and SARS-CoV-2 infection, in accordance with some embodiments.

Reporter transcriptional reporter assays were utilized to find that MASL inhibited STAT3 and NFκB signaling activity in a dose responsive manner as shown in FIG. 18A.

Figure 16C:
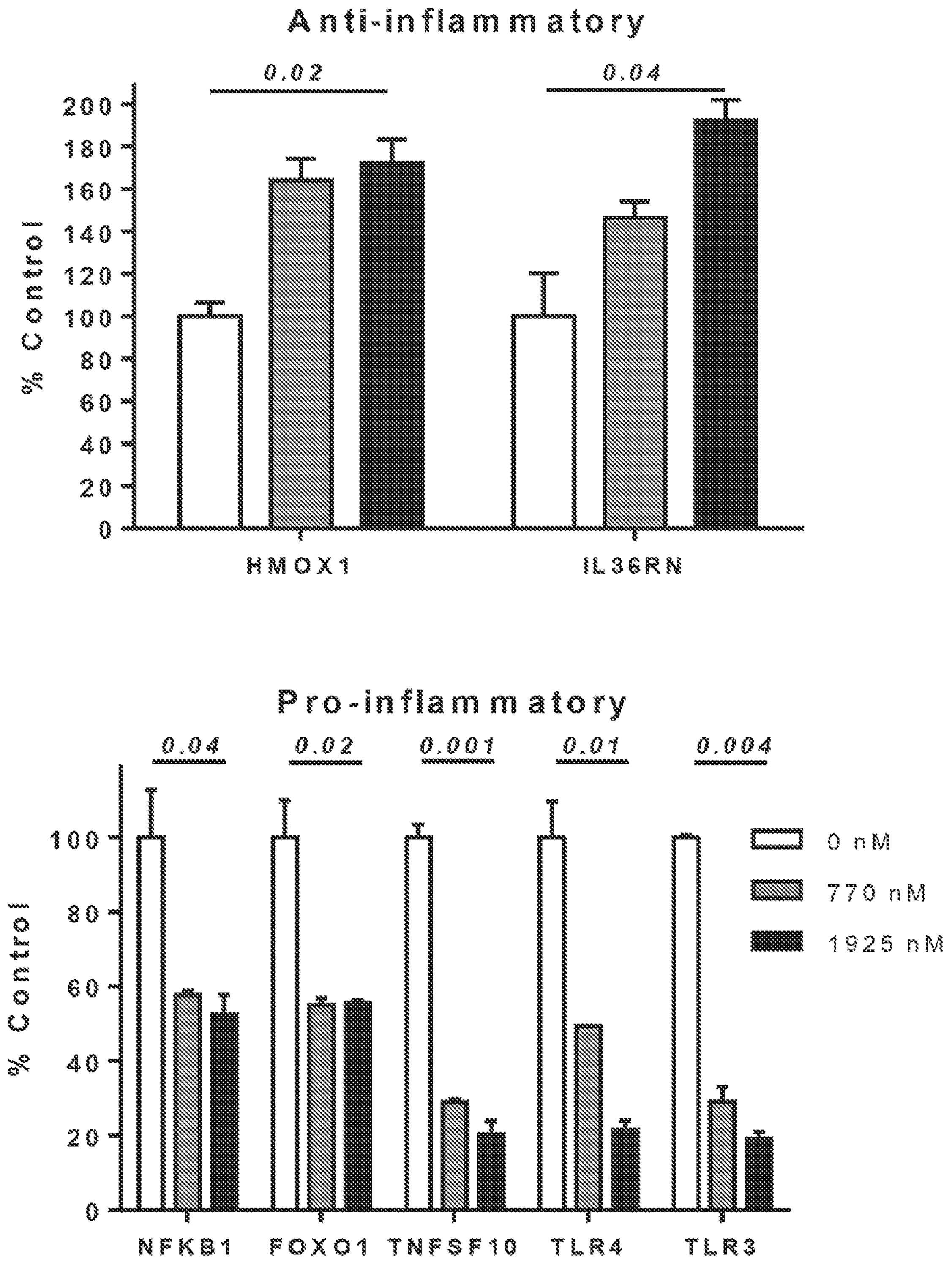

NF-KB regulates cytokine expression and inflammatory immune response to infection. Accordingly, NF-kB signaling has been implicated in the control of ACE2 expression and COVID-19 inflammatory pathologies. If left unchecked, these infections induce FOXO1 expression in epithelial cells including oral mucosa, which induces the expression of toll-like receptors (TLRs). TLR signaling induces interleukin-36 (IL36) production, which induces IL6 expression. IL6 then goes on to produce inflammatory cytokines in response to infections including tuberculosis in lung epithelial cells. Heme oxygenase 1 (HMOX1) induces IL36RN expression, which acts as an IL36 antagonist to inhibit inflammation. As shown in FIG. 16C, MASL increased both HMOX1 and IL36RN mRNA expression in a dose responsive manner. These data suggest that MASL utilizes HMOX1 to induce IL36RN expression. Along with increasing the expression of anti-inflammatory mediators, MASL also decreased the expression of mRNA encoding inflammatory transcription factors NFκB and FOXO1, as well as the inflammatory cytokine TNFSF10, and toll-like receptors TLR3 and TLR4 in a dose responsive manner as shown in FIG. 16C.

Figure 18B:
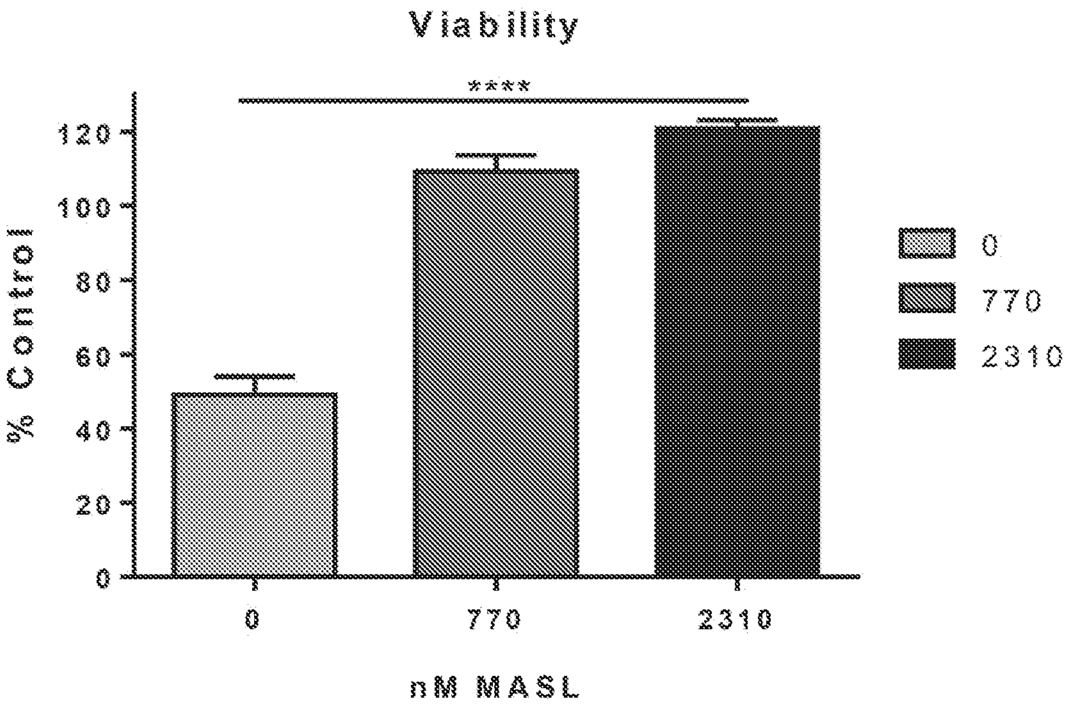

An established assay was used to investigate the effect of MASL on SARS-COV-2 infection. As shown in FIG. 18B, 770 nM and 1925 nM MASL significantly decreased viral toxicity in a dose responsive manner. These data indicate that MASL can inhibit the ability of the SARS-CoV-2 virus to infect mammalian cells.

Example 2-2: Discussion on the comprehensive study

SARS-CoV-2 kills about 2% of infected individuals. This mortality rate is over 10 times higher than that of the seasonal influenza virus. Remdesivir is currently approved to treat COVID-19 and other drugs and vaccines are currently being deployed. However, over 33,000 COVID-19 related deaths were reported in the United States during February of 2021. There is a clear need for new COVID-19 treatment options.

Severe acute respiratory distress syndrome (ARDS) is a major COVID-19 morbidity. COVID-19 instigates chronic inflammation resulting in a "cytokine storm" that causes most ARDS mediated deaths. COVID-19 also causes multisystem inflammatory syndrome (MIS) in children and adolescents. This hyper-inflammation leads to multiple organ failure and shock. Treatments for these inflammatory syndromes include parenteral immunoglobulin and steroids with limited efficacy. The IL-6 antibody blocker tocilizumab was found an effective treatment for CAR-T cell induced cytokine storm, and has been adopted as a treatment for COVID-19 inflammation.

Figure 18C:
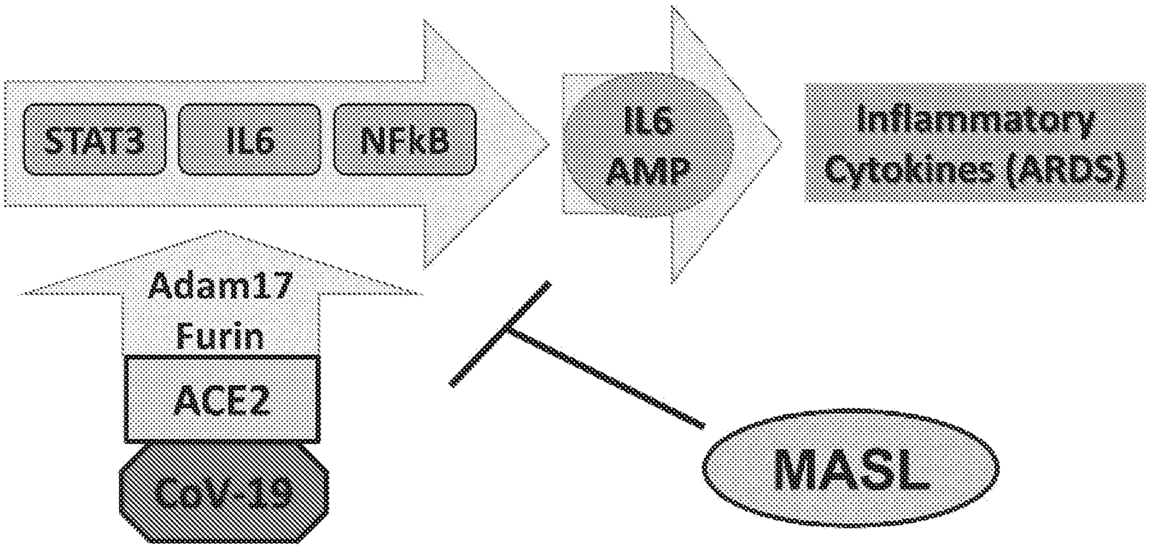

Unlike antibodies, lectins can be taken orally to treat diseases including cancer and viral infections. MASL targets sialic acid modified receptors to inhibit cancer progression and inflammation. Results from the present study indicate that MASL inhibits ACE2 expression, SARS-CoV-2 spike binding, and major components of the IL6 amplifier including STAT3, IL6, and NFκB as illustrated in FIG. 18C. In addition to viral lung inflammation, IL6 signaling also triggers contact dermatitis and psoriasis in keratinocytes, as well as arthritic inflammation in chondrocytes. COVID-19 inflammation shares inflammatory mechanisms with arthritis. Indeed, COVID-19 infection causes arthralgia and myalgia in 15% and 44% of patients, respectively. MASL attenuates inflammatory NFκB signaling and inflammation in chondrocyte cell culture, and can be administered orally to alleviate arthritis progression in mice. In addition, MASL also suppresses interleukin induced psoriatic inflammation in reconstituted epidermis. Taken together, data indicate that MASL can be used alone or in combination with other antiviral and anti-inflammatory agents for COVID-19 treatment.

The terms and expressions employed herein are used as terms of description and not of limitation, and there is no intention in the use of such terms and expressions of excluding any equivalents of the features shown and described or portions thereof, but it is recognized that various modifications are possible within the scope of the embodiments of the present application. Thus, it should be understood that although the present application describes specific embodiments and optional features, modification and variation of the compositions, methods, and concepts herein disclosed may be resorted to by those of ordinary skill in the art, and that such modifications and variations are considered to be within the scope of embodiments of the present application.

SEQUENCE LISTING:

```
SEQ ID NO: 1 Maackia amurensis seed lectin (MASL)
Ser Asp Glu Leu Ser Phe Thr Ile Asn Asn Phe Val Pro Asn Glu
Ala
```

-continued

| SEQUENCE LISTING: |
|---|
| Asp Leu Leu Phe Gln Gly Glu Ala Ser Val Ser Ser Thr Gly Val Leu<br>Gln Leu Thr Arg Val Glu Asn Gly Gln Pro Gln Gln Tyr Ser Val Gly<br>Arg Ala Leu Tyr Ala Ala Pro Val Arg Ile Trp Asp Asn Thr Thr Gly<br>Ser Val Ala Ser Phe Ser Thr Ser Phe Thr Phe Val Val Lys Ala Pro<br>Asn Pro Thr Ile Thr Ser Asp Gly Leu Ala Phe Phe Leu Ala Pro Pro<br>Asp Ser Gln Ile Pro Ser Gly Arg Val Ser Lys Tyr Leu Gly Leu Phe<br>Asn Asn Ser Asn Ser Asp Ser Ser Asn Gln Ile Val Ala Val Glu Phe<br>Asp Thr Tyr Phe Gly His Ser Tyr Asp Pro Trp Asp Pro Asn Tyr Arg<br>His Ile Gly Ile Asp Val Asn Gly Ile Glu Ser Ile Lys Thr Val Gln<br>Trp Asp Trp Ile Asn Gly Gly Val Ala Phe Ala Thr Ile Thr Tyr Leu<br>Ala Pro Asn Lys Thr Leu Ile Ala Ser Leu Val Tyr Pro Ser Asn Gln<br>Thr Ser Phe Ile Val Ala Ala Ser Val Asp Leu Lys Glu Ile Leu Pro<br>Glu Trp Val Arg Val Gly Phe Ser Ala Ala Thr Gly Tyr Pro Thr Gln<br>Val Glu Thr His Asp Val Leu Ser Trp Ser Phe Thr Ser Thr Leu Glu<br>Ala Asn Cys Asp Ala Ala Thr Glu Asn |
| SEQ ID NO: 2 DNA sequence for Stat3 transcriptional reporter assays<br>TGCTTCCCGAATTCCCGAATTCCCGAATTCCCGAATTCCCGAATTCCCGAACGT |
| SEQ ID NO: 3 DNA sequence for NFkB transcriptional reporter assays<br>GCTACAAGGGACTTTCCGCTGGGGACTTTCCAGG |

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of treating a SARS-COV-2 infection in a subject in need thereof, the method comprising administering to the subject a pharmaceutical composition comprising at least one pharmaceutically acceptable carrier and a therapeutically effective amount of *Maackia amurensis* seed lectin (MASL).

2. The method of claim 1, wherein the MASL comprises the amino acid sequence of SEQ ID NO:1.

3. The method of claim 1, further comprising administering to the subject a therapeutically effective amount of a second agent effective for treating the SARS-COV-2 infection.

4. The method of claim 3, wherein the second agent comprises at least one selected from an antiviral agent, an anti-SARS-COV-2 antibody, and an immunomodulator.

5. The method of claim 1, wherein the SARS-COV-2 infection causes cytokine storm or acute respiratory distress syndrome (ARDS) in the subject.

6. The method of claim 1, wherein the subject is a human.

* * * * *

SEQUENCE LISTING

```
<160> NUMBER OF SEQ ID NOS: 3

<210> SEQ ID NO 1
<211> LENGTH: 249
<212> TYPE: PRT
<213> ORGANISM: Maackia amurensis

<400> SEQUENCE: 1

Ser Asp Glu Leu Ser Phe Thr Ile Asn Asn Phe Val Pro Asn Glu Ala
1               5                   10                  15

Asp Leu Leu Phe Gln Gly Glu Ala Ser Val Ser Ser Thr Gly Val Leu
            20                  25                  30

Gln Leu Thr Arg Val Glu Asn Gly Gln Pro Gln Gln Tyr Ser Val Gly
        35                  40                  45

Arg Ala Leu Tyr Ala Ala Pro Val Arg Ile Trp Asp Asn Thr Thr Gly
    50                  55                  60

Ser Val Ala Ser Phe Ser Thr Ser Phe Thr Phe Val Val Lys Ala Pro
65                  70                  75                  80

Asn Pro Thr Ile Thr Ser Asp Gly Leu Ala Phe Phe Leu Ala Pro Pro
                85                  90                  95
```

-continued

```
Asp Ser Gln Ile Pro Ser Gly Arg Val Ser Lys Tyr Leu Gly Leu Phe
            100                 105                 110

Asn Asn Ser Asn Ser Asp Ser Ser Asn Gln Ile Val Ala Val Glu Phe
        115                 120                 125

Asp Thr Tyr Phe Gly His Ser Tyr Asp Pro Trp Asp Pro Asn Tyr Arg
    130                 135                 140

His Ile Gly Ile Asp Val Asn Gly Ile Glu Ser Ile Lys Thr Val Gln
145                 150                 155                 160

Trp Asp Trp Ile Asn Gly Gly Val Ala Phe Ala Thr Ile Thr Tyr Leu
                165                 170                 175

Ala Pro Asn Lys Thr Leu Ile Ala Ser Leu Val Tyr Pro Ser Asn Gln
            180                 185                 190

Thr Ser Phe Ile Val Ala Ala Ser Val Asp Leu Lys Glu Ile Leu Pro
        195                 200                 205

Glu Trp Val Arg Val Gly Phe Ser Ala Ala Thr Gly Tyr Pro Thr Gln
    210                 215                 220

Val Glu Thr His Asp Val Leu Ser Trp Ser Phe Thr Ser Thr Leu Glu
225                 230                 235                 240

Ala Asn Cys Asp Ala Ala Thr Glu Asn
                245


<210> SEQ ID NO 2
<211> LENGTH: 54
<212> TYPE: DNA
<213> ORGANISM: Artificial Sequence
<220> FEATURE:
<223> OTHER INFORMATION: DNA sequence for Stat3 transcriptional reporter
      assays

<400> SEQUENCE: 2

tgcttcccga attcccgaat tcccgaattc ccgaattccc gaattcccga acgt           54


<210> SEQ ID NO 3
<211> LENGTH: 34
<212> TYPE: DNA
<213> ORGANISM: Artificial Sequence
<220> FEATURE:
<223> OTHER INFORMATION: DNA sequence for NFkB transcriptional reporter
      assays

<400> SEQUENCE: 3

gctacaaggg actttccgct ggggactttc cagg                                 34
```